US012569363B1

(12) United States Patent
Hanrahan et al.

(10) Patent No.: US 12,569,363 B1
(45) Date of Patent: Mar. 10, 2026

(54) PORTABLE SYSTEM INCLUDING POST-SURGICAL BRACE WITH ANTI-INFLAMMATION COOLING

(71) Applicant: Vibe Wellness, LLC, Holladay, UT (US)

(72) Inventors: Megan C. Hanrahan, Holladay, UT (US); Christine Decaria, Holladay, UT (US); Arianna Phillips, Holladay, UT (US); Josh Conarton, Salt Lake City, UT (US); Michael J. McMahon, Sandy, UT (US)

(73) Assignee: Vibe Wellness, LLC, Holladay, UT (US)

( * ) Notice: Subject to any disclaimer, the term of this patent is extended or adjusted under 35 U.S.C. 154(b) by 424 days.

(21) Appl. No.: 17/982,335

(22) Filed: Nov. 7, 2022

Related U.S. Application Data

(63) Continuation-in-part of application No. 16/023,773, filed on Jun. 29, 2018, now abandoned.

(Continued)

(51) Int. Cl.
| | |
|---|---|
| *A61F 5/01* | (2006.01) |
| *A61F 5/37* | (2006.01) |

(Continued)

(52) U.S. Cl.
CPC .......... *A61F 5/0109* (2013.01); *A61F 5/3761* (2013.01); *A61F 7/10* (2013.01);

(Continued)

(58) Field of Classification Search
CPC .... A61F 5/0109; A61F 5/0123; A61F 5/0125; A61F 5/0585; A61F 5/0102;

(Continued)

(56) References Cited

U.S. PATENT DOCUMENTS

| | | |
|---|---|---|
| 4,886,053 A | 12/1989 | Neal |
| 5,170,783 A | 12/1992 | Smith |

(Continued)

OTHER PUBLICATIONS

Aircast "Cryo/Cuff IC: Automatic Integrated Compression and CyroTherapy System" Accessed Feb. 2, 2023 from URL: https://mycoldtherapy.com/collections/aircast, 1 page.

(Continued)

*Primary Examiner* — Adam Baker
(74) *Attorney, Agent, or Firm* — Workman Nydegger

(57) ABSTRACT

The product here defined is a modular knee brace system that includes a knee brace, and which may include one or more modules, where the system is portable. The knee brace is configured specifically for recovery from injury, or surgery. The knee brace includes a breathable shell layer for providing support around the knee of the user. The brace may include a removable insert, which may be relatively rigid for insertion into a pocket of the knee brace to provide extension (e.g., terminal extension) of the knee when the insert is inserted. Heating and/or cooling is also provided. The system may further include a portable elevation stand, allowing the user to elevate the lower leg during cooling or heating treatment. The system may utilize AI driven custom printed components to uniquely address individual patients' treatment and healing plans.

22 Claims, 28 Drawing Sheets

Related U.S. Application Data

(60) Provisional application No. 62/691,875, filed on Jun. 29, 2018, provisional application No. 62/599,167, filed on Dec. 15, 2017, provisional application No. 62/526,592, filed on Jun. 29, 2017.

(51) Int. Cl.
*A61F 7/10* (2006.01)
*A61F 7/00* (2006.01)

(52) U.S. Cl.
CPC ................. *A61F 2007/0042* (2013.01); *A61F 2007/0056* (2013.01)

(58) Field of Classification Search
CPC .... A61F 5/0106; A61F 5/012; A61F 5/05816; A61F 5/30; A61F 5/34; A61F 2007/0042; A61F 2007/0054; A61F 2007/0056; A61F 2007/0057; A61F 7/065; A61F 7/075; A61F 7/0755; A61F 7/1082; A61F 7/1096; A61F 7/109; A47C 16/02; A61G 13/10; A61G 13/12; A61G 13/1235; A61G 13/1245; A61G 13/1285; A61G 13/128; A61G 13/129; A61G 13/101; A61G 13/1205–1255; A61G 13/0036; A61G 13/0063
USPC ............................................................ 602/2
See application file for complete search history.

(56) References Cited

U.S. PATENT DOCUMENTS

| | | | |
|---|---|---|---|
| 5,230,335 A | | 7/1993 | Johnson et al. |
| 5,277,695 A | | 1/1994 | Johnson et al. |
| 5,314,455 A | | 5/1994 | Johnson et al. |
| 5,318,068 A | * | 6/1994 | Haugen ................... A61H 3/02 |
| | | | 135/66 |
| 5,413,142 A | | 5/1995 | Johnson et al. |
| 5,415,624 A | | 5/1995 | Williams |
| 6,178,562 B1 | | 1/2001 | Elkins |
| 6,336,909 B2 | | 1/2002 | Gildersleeve et al. |
| 6,409,691 B1 | | 6/2002 | Dakin et al. |
| D473,315 S | | 4/2003 | Miros et al. |
| D473,656 S | | 4/2003 | Miros et al. |
| D473,948 S | | 4/2003 | Elkins et al. |
| D476,996 S | | 7/2003 | Amit et al. |
| D477,413 S | | 7/2003 | Schirrmacher |
| 6,695,872 B2 | | 2/2004 | Elkins |
| 6,871,878 B2 | | 3/2005 | Miros |
| D504,727 S | | 5/2005 | Schirrmacher et al. |
| 7,198,093 B1 | | 4/2007 | Elkins |
| D559,393 S | | 1/2008 | Schirrmacher |
| D566,908 S | | 4/2008 | Schirrmacher et al. |
| D572,044 S | | 7/2008 | Miros |
| D574,019 S | | 7/2008 | Amit et al. |
| 7,744,551 B2 | | 6/2010 | Pick et al. |
| 7,837,638 B2 | | 11/2010 | Miros et al. |
| 7,892,195 B2 | | 2/2011 | Grim et al. |
| 7,896,910 B2 | | 3/2011 | Schirrmacher et al. |
| 7,959,657 B1 | * | 6/2011 | Harsy ..................... A61F 7/007 |
| | | | 607/104 |
| 8,043,242 B2 | | 10/2011 | Mcspadden et al. |
| 8,282,588 B2 | | 10/2012 | Ingimundarson et al. |
| 8,425,579 B1 | | 4/2013 | Edelman et al. |
| 8,672,864 B2 | | 3/2014 | Nordt et al. |
| 8,715,330 B2 | | 5/2014 | Lowe et al. |
| 10,231,860 B2 | | 3/2019 | Forbes et al. |
| 2005/0256556 A1 | | 11/2005 | Schirrmacher et al. |
| 2006/0135903 A1 | | 6/2006 | Ingimundarson et al. |
| 2006/0206045 A1 | | 9/2006 | Townsend et al. |
| 2007/0161932 A1 | * | 7/2007 | Pick .......................... A61F 7/08 |
| | | | 602/5 |
| 2009/0312681 A1 | * | 12/2009 | McSpadden .......... A61F 5/0123 |
| | | | 602/2 |
| 2010/0018537 A1 | * | 1/2010 | Soto ........................ A61G 13/12 |
| | | | 128/845 |
| 2010/0057171 A1 | | 3/2010 | Stephens |
| 2012/0290102 A1 | | 11/2012 | Mahoney |
| 2013/0006154 A1 | * | 1/2013 | Lowe ................... A61H 9/0092 |
| | | | 607/104 |
| 2013/0085420 A1 | * | 4/2013 | Feinstein ............. A61N 1/0468 |
| | | | 601/5 |
| 2013/0331914 A1 | * | 12/2013 | Lee ......................... A61F 7/007 |
| | | | 607/96 |
| 2014/0222121 A1 | | 8/2014 | Spence et al. |
| 2014/0228718 A1 | | 8/2014 | Diller et al. |
| 2014/0330184 A1 | | 11/2014 | Kilbey |
| 2015/0018733 A1 | * | 1/2015 | Ben-Meir ................. A61F 5/01 |
| | | | 602/6 |
| 2015/0290014 A1 | * | 10/2015 | Anglada ............... A61F 5/0125 |
| | | | 602/26 |
| 2015/0328016 A1 | * | 11/2015 | Summit ................. A61F 5/013 |
| | | | 703/1 |

OTHER PUBLICATIONS

Donjoy "Playmaker Knee Ligament Brace" Accessed Feb. 2, 2023 from URL https://www.donjoyperformance.com/donjoy-playmaker-knee-brace 1 page.

Final Office Action received for U.S. Appl. No. 16/023,773, mailed on Jul. 5, 2022, 22 pages.

Final Rejection Mailed on Feb. 8, 2021 for U.S. Appl. No. 16/023,773.

Non-Final Office Action received for U.S. Appl. No. 16/023,773, mailed on Aug. 11, 2020.

Non-Final Rejection Mailed on Dec. 21, 2021 for U.S. Appl. No. 16/023,773.

* cited by examiner

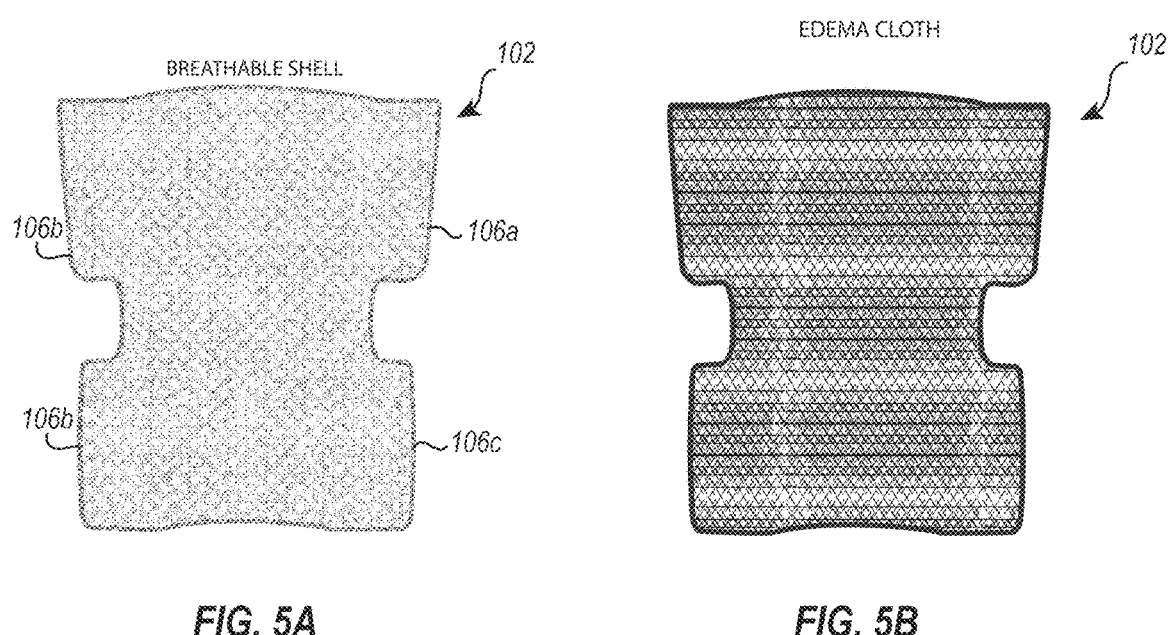
FIG. 5A
FIG. 5B
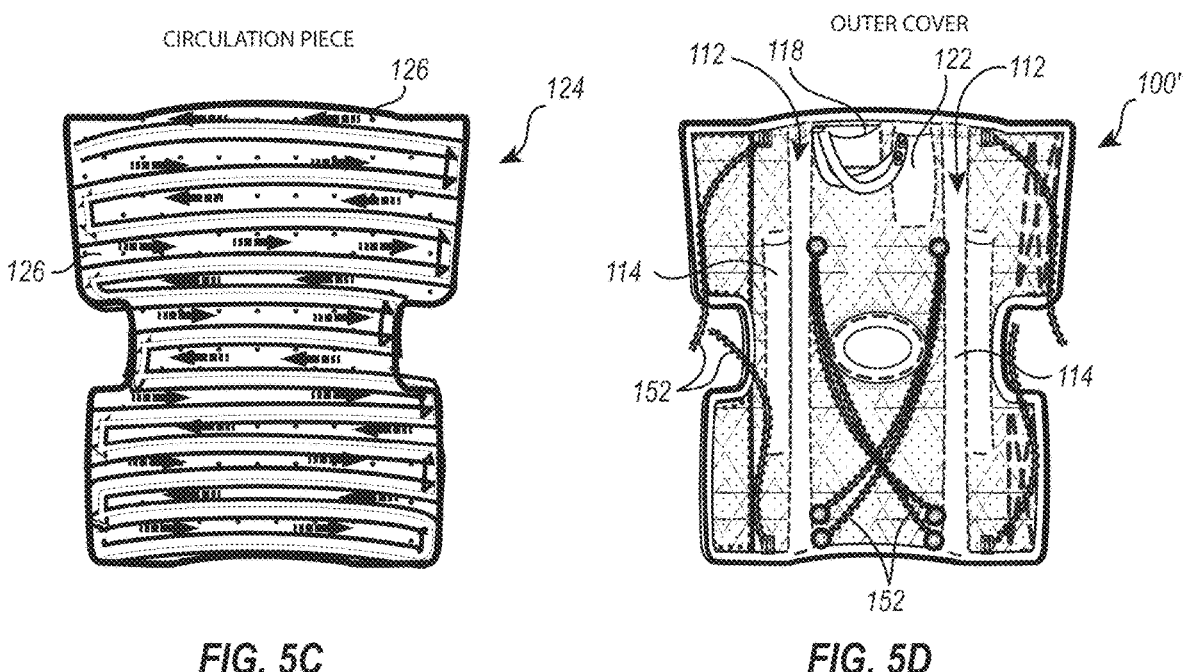
FIG. 5C
FIG. 5D

EDEMA CLOTH                                    102

CIRCULATION PIECE                             124

RUBBER INSERT DESIGN                          128

112  118  OUTER COVER  122  112  100'

152

152                                          114

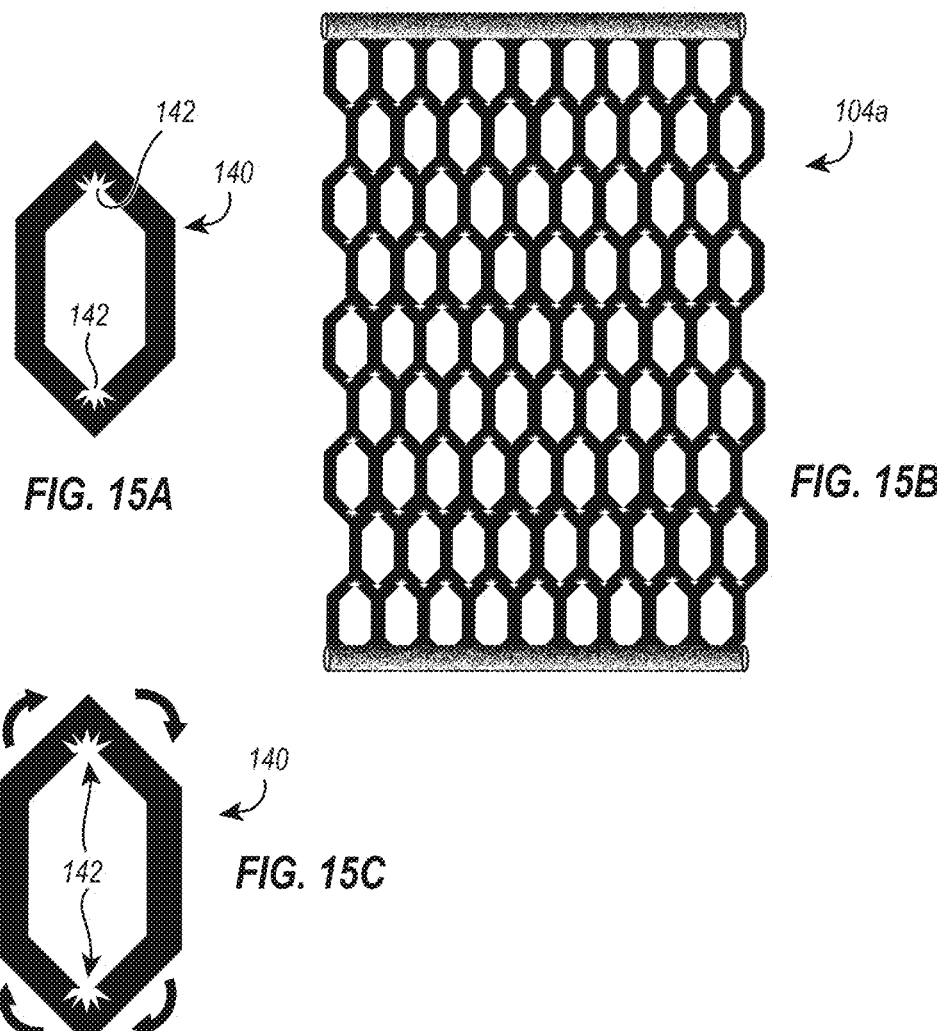
FIG. 15A
FIG. 15B
FIG. 15C
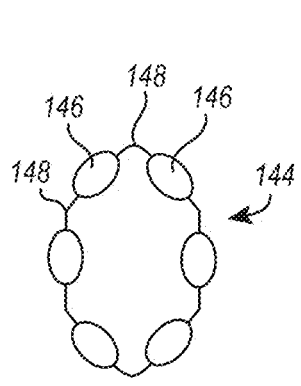
FIG. 15D
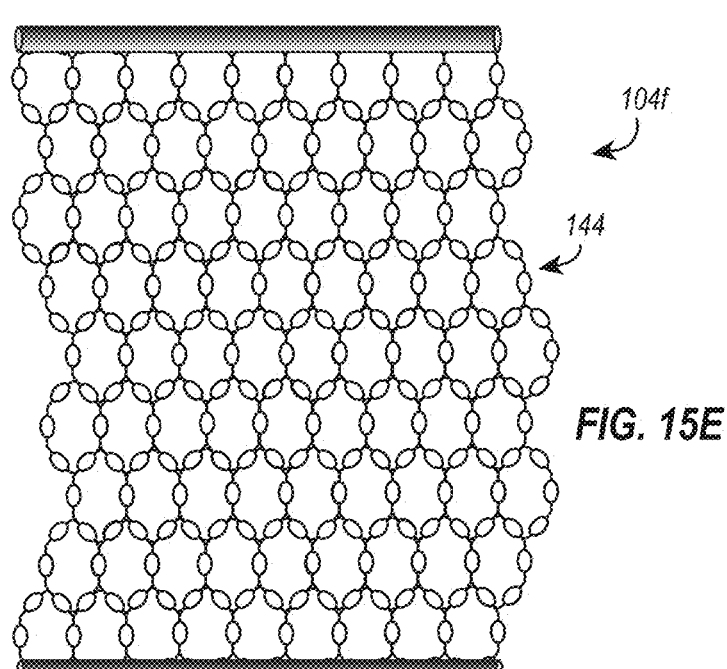
FIG. 15E

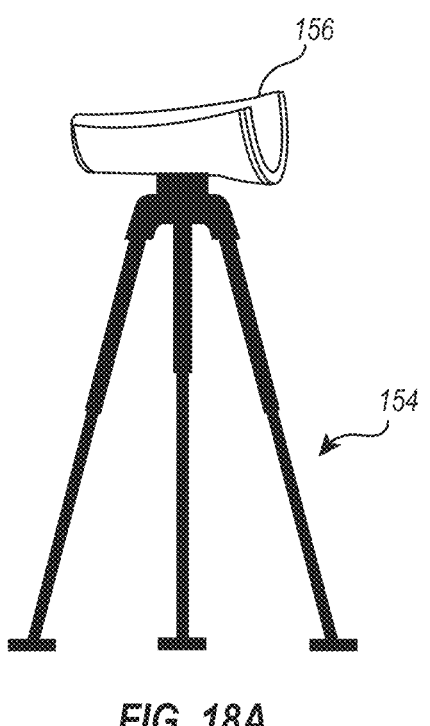
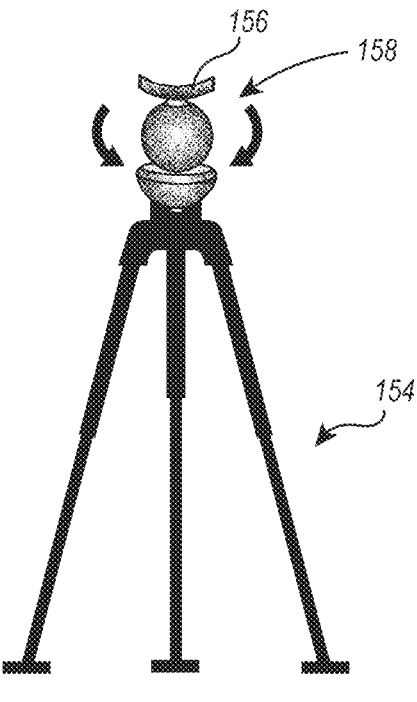
FIG. 18A          FIG. 18B
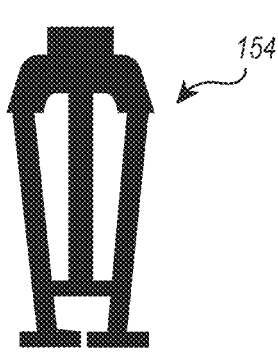
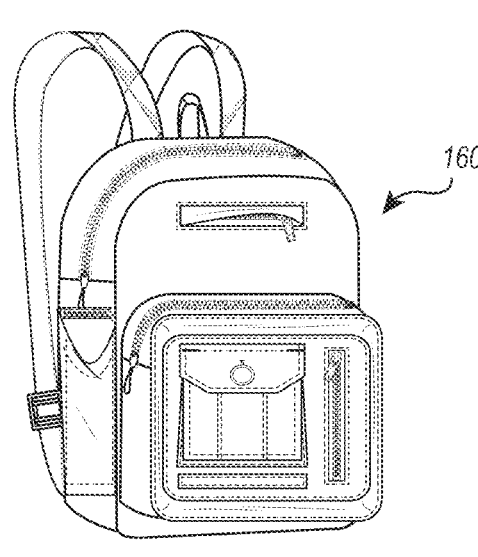
FIG. 19          FIG. 20

2500

2502 — Accessing A Diagnostic Model

2504 — Obtaining A Set Of Considerations

2506 — Applying The Set Of Considerations To The Diagnostic Model

2508 — Receiving A Set Of Determinations From The Diagnostic Model

2510 — Creating A Knee Brace Based On The Set Of Determinations

2600

2602 Accessing A Real-Time Model

2604 Obtaining A Second Set Of Considerations

2606 Applying The Second Set Of Considerations To The Real-Time Model

2608 Receiving A Second Set Of Determinations From The Real-Time Model

2610 Reconfiguring The Knee Brace Based On The Second Set Of Determinations

PORTABLE SYSTEM INCLUDING POST-SURGICAL BRACE WITH ANTI-INFLAMMATION COOLING

CROSS-REFERENCE TO RELATED APPLICATIONS

This application is a continuation-in-part under 35 U.S.C. 120 of U.S. patent application Ser. No. 16/023,773 filed Jun. 29, 2018, which claims priority to and the benefit of U.S. Provisional Patent Application Ser. Nos. 62/526,592; 62/599,167; and 62/691,875 filed on Jun. 29, 2017; Dec. 15, 2017, and Jun. 29, 2018, respectively. Each of the foregoing applications is incorporated herein by reference in its entirety.

BACKGROUND

When a patient undergoes knee surgery, injures the knee, or has a disease that affects the knee such as osteoarthritis, often the recovery treatment includes application of a knee brace about the knee to support the knee during recovery. It is also common to prescribe opiate pain medications during such periods of knee recovery, which opiates can be notoriously addictive. While icing of the knee and surrounding area can be helpful in aiding control of pain during the recovery period, such icing requires near constant attention to re-apply the ice periodically, to properly elevate the knee, and the like. As a result, the recovery process is very cumbersome and difficult. There is a continuing need for improved post-surgical or post injury knee braces that might reduce the need for opiate pain medications, and that might more conveniently and inexpensively provide for pain management and decrease inflammation.

BRIEF SUMMARY

The product here defined is a medical device, specifically a sophisticated, multiple modality medical device. It is specifically a lower limb, knee brace for recovery from lower extremity injury to the knee and surrounding structures. Such brace and related methods described herein may be useful in recovery from events such as, but not limited to: ACL tear and ligament reconstruction; other knee ligament tears such as PCL, medial or lateral collateral ligaments and possible reconstruction or repair; meniscal tear and/or repair; patellar dislocation or fracture or crush injury with or without surgical management, tibial plateau fracture, stem cell/plasma treatment; or other evolving regenerative medicine procedures.

The present knee brace has alignment, postural support, and external stability based on a "tensegrity" architecture, where tensegrity is defined as the balance of tension and strength. Tensegrity is applied in the construction and design of the present device.

The knee brace also uses the POST model where POST refers to postural orthopaedic support tensegrity. It approaches the musculoskeletal ("MSK") model as a symmetry of balance, suspension of bones in space, held by the fascia, muscular tension, and ligamentous structures. Previous models in the past have modeled the human body more as a stacking or loading of structure (bones) on top of each other. Based on this model, most casts, braces, supports, and wraps create a relatively static or "held" model of support, rather than one that provides for and permits dynamic suspension of the supported structures. For example by way of analogy, one might picture a bridge, such as a suspension bridge that allows for vibration, weight, compression, etc. but also exhibits some fluidity and flow. The present brace may thus include structure that exhibits strong tensegrity balance rather than relatively rigid brace structures that rigidly hold, compress, and/or squash.

In an embodiment, the system may be portable, and may include a knee brace, as well as various modules that may be used therewith, as will be explained herein. The system may thus be designed to be portable, and allow a user to select particular modules they wish to use with the knee brace at any particular time. By way of example, the knee brace may include a breathable shell layer configured to provide support around the knee of a user. Such shell may have tensegrity and/or POST features included therein, e.g., in the form of specific materials employed, patterns or geometries used, and the like. The knee brace device may also include a removable relatively rigid insert that is positionable along the back of the knee during use, to provide extension of the knee when the insert is inserted into the knee brace. For example, such an insert may be insertable into a pocket formed in the shell layer of the brace.

In another embodiment, the insert could be permanently integrated into the knee brace, although the ability to remove the insert is helpful, e.g., allowing the user to insert the insert when full "terminal knee extension" or other sub-terminal extension of the knee is desired. This also allows the user to remove the insert, so that the knee can then bend back away from the 0° terminal extension point, allowing the user to move the knee and perhaps participate to some extent in various activities that would require knee flexion (e.g., walking, climbing a flight of stairs, transferring in and out of the car). In embodiments in which the rigid member which rests behind the knee is permanently (rather than removably) positioned, such rigid member may include a hinge structure, which may allow a user to perform flexion of the knee, when the hinge is active. The hinge may be adjustable in a manner to allow the user to prevent knee flexion, forcing the device in that configuration to serve as a knee immobilizer. It will be apparent that various configurations of such an insert or rigid member are possible.

The knee brace may also include cooling means provided in the knee brace for providing coolant to the knee to reduce inflammation in the user's knee during use. It will also be appreciated that heating means may additionally or alternatively be provided. For example, in some embodiments, cycling between application of heating and cooling, one after the other, for a given time may be helpful in healing. The knee brace may accommodate such treatment.

In an embodiment, the cooling means may comprise flaccid lay-flat tubing that may be provided in the knee brace for carrying coolant pumped from a coolant pump and reservoir, so as to circulate coolant through the knee brace. In such embodiments, the system may include such a coolant pump and/or reservoir. Where heating is provided, a heat source could be provided, as desired. Power for providing such heat, or for circulating a coolant or a heating fluid could be provided by a rechargeable battery or other mechanism. For example, such a rechargeable battery may provide for 6 hours of use.

The knee brace system may also include an elevation stand for elevating the lower leg of the user, below the knee, better facilitating a generally horizontal disposition of the leg of the user, with the knee at terminal extension (or possibly some sub-terminal extension). Such an elevation stand may be in the form of a bipod, tripod, monopod, or other support that may be selectively attachable to the knee brace, allowing a user to more easily elevate the knee and lower leg when the elevation stand is attached thereto.

Some embodiments may additionally be optimized for a unique patient by the use of AI driven custom printed components. The AI model may include a diagnostic model and/or a real-time model. The diagnostic model may be used to custom create a brace which is designed specifically based on the unique patients pre-existing medical necessities and treatment plan. The real-time model may be used to monitor patient treatment remotely or before, during, and/or after physical therapy and/or healing.

While various devices may be currently available that may provide some of the benefits provided by the present invention, none of them provide the various components in a modular configuration as described herein, which allows a user to select particular system components for a particular time of use, e.g., leaving various other components at home or the office, which may be selected for use at another time. Some embodiments of the invention provide a knee brace that may be dynamically configured and tuned to a unique patient's treatments, therapy, and/or needs. The knee brace may be further reconfigured and tuned at multiple points in time as a patient's needs change. This allows for an adaptable and customizable knee brace (as referred to as a living brace).

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings.

FIGS. 5A-5D show an exemplary breathable shell, an edema cloth layer, a circulation piece, and the outer cover, respectively.

FIG. 15A schematically illustrates a geometric design similar to that seen in FIG. 8, which includes a living hinge, and which may be used to provide dimensional stability to portions of the knee brace.

FIG. 15B illustrates how the geometric design of FIG. 15A can be arranged in an array for providing dimensional stability to desired portions of the knee brace.

FIG. 15C schematically illustrates some of the dimensional flexibility and stability movements possible with the geometric design of FIG. 15A.

FIG. 15D schematically illustrates another geometric design that includes living hinge elements, which may be used to provide dimensional stability to portions of the knee brace.

FIG. 15E illustrates how the geometric design of FIG. 15D can be arranged in an array for providing dimensional stability to desired portions of the knee brace.

FIG. 18A illustrates an exemplary elevation stand for attachment to and/or use with the knee brace, for elevating the knee of the user.

FIG. 18B shows an elevation stand similar to that of FIG. 18A, showing how a ball joint may be provided therewith.

FIG. 19 illustrates how the elevation stand may be folded up or otherwise collapsible, for easy storage and portability.

FIG. 20 illustrates a backpack which may be used with the remainder of the knee brace system for storage and portability of the various modules included with the system.

5

Figure 27:
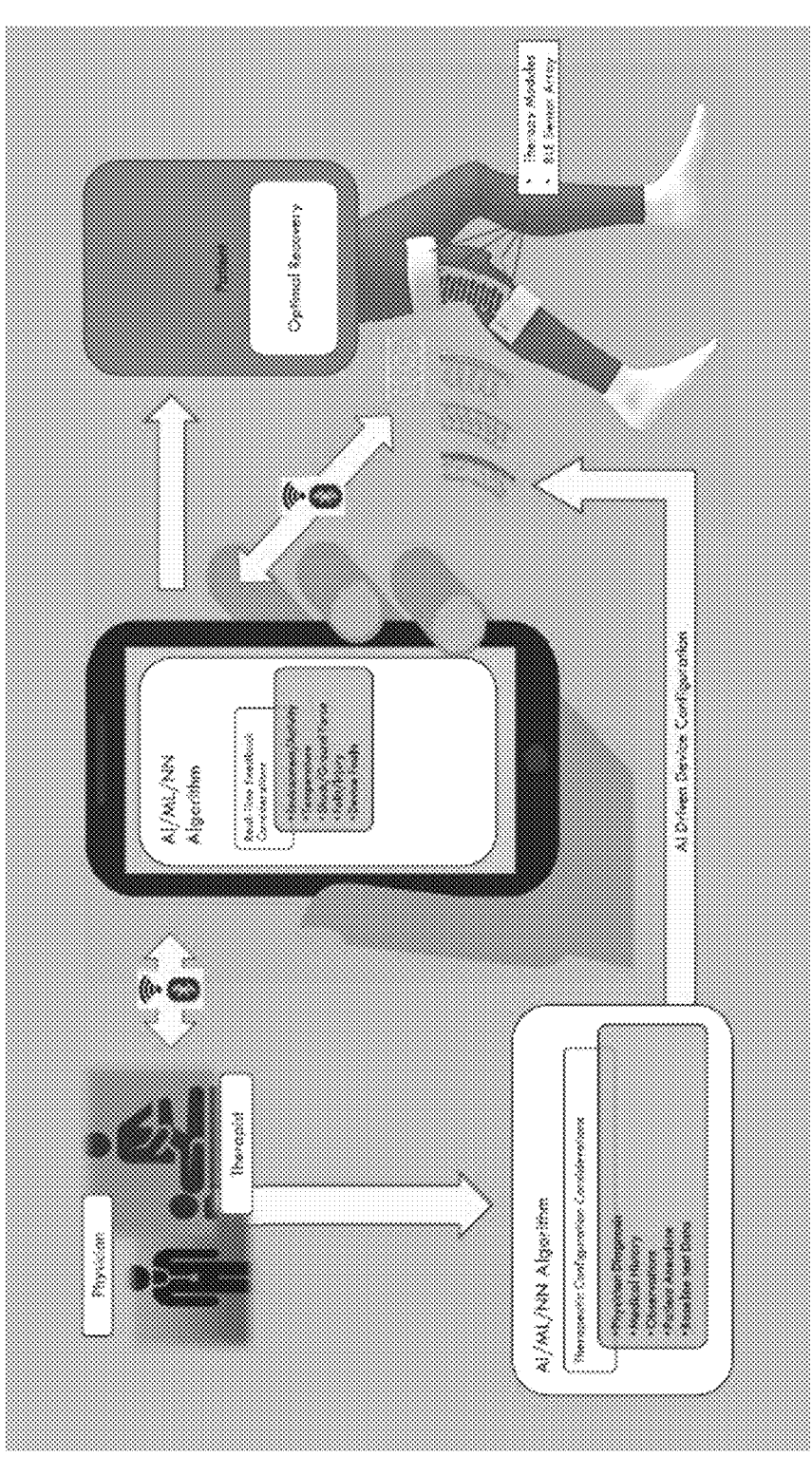
Figure 28B:
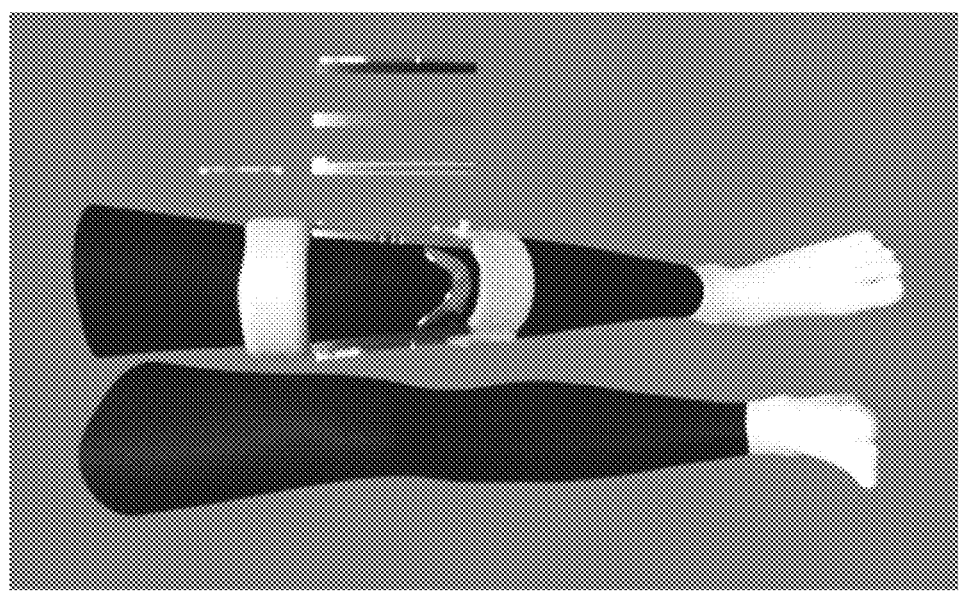
Figure 28A:
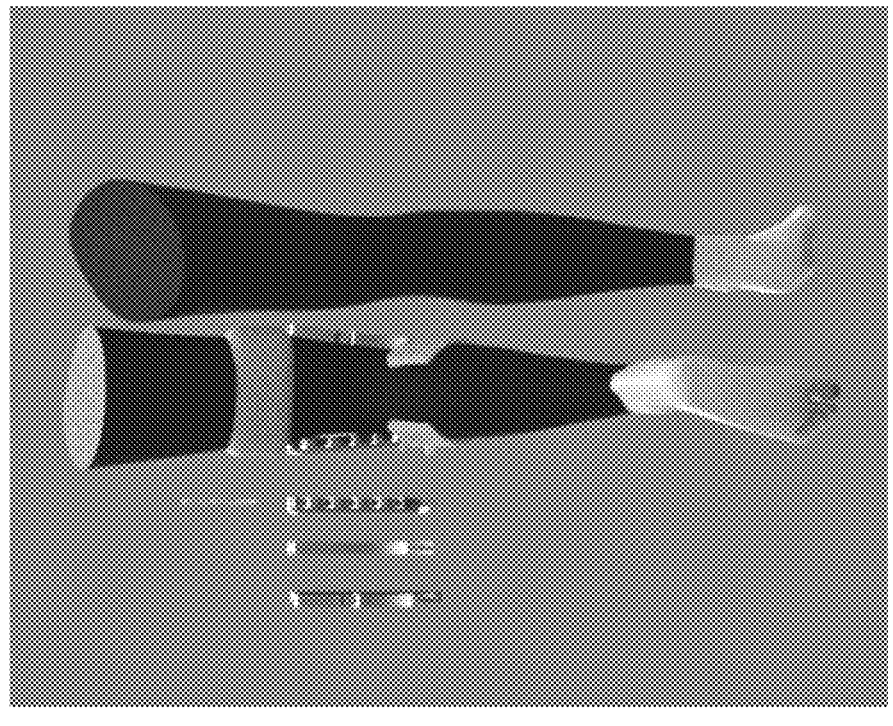
Figure 28D:
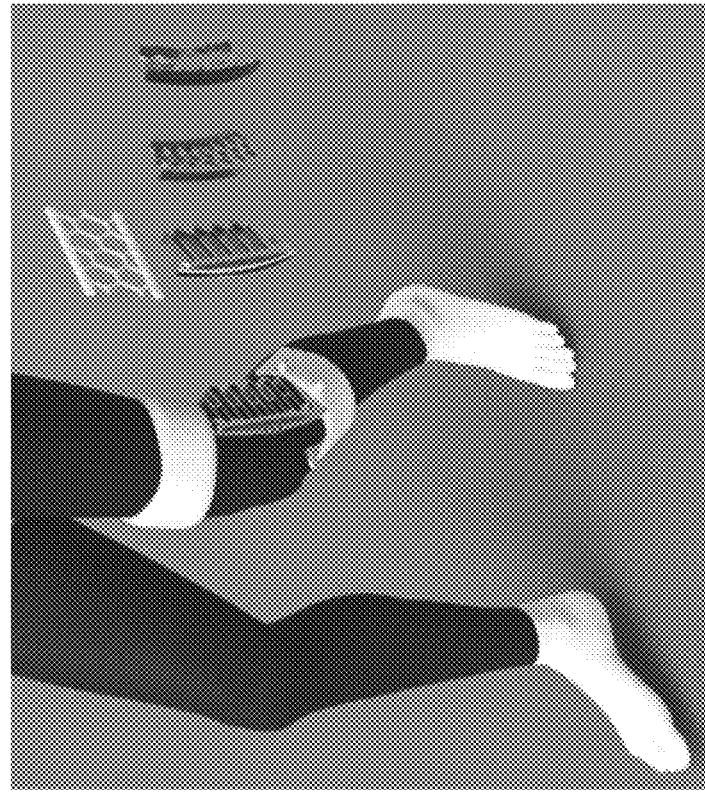
Figure 28C:
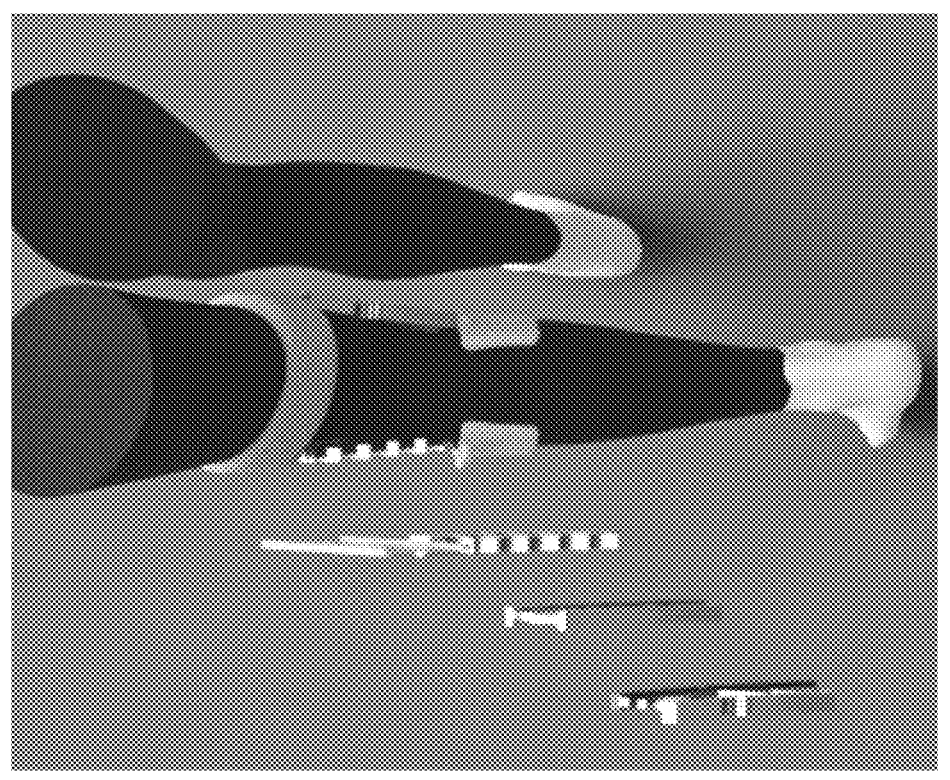
Figure 28E:
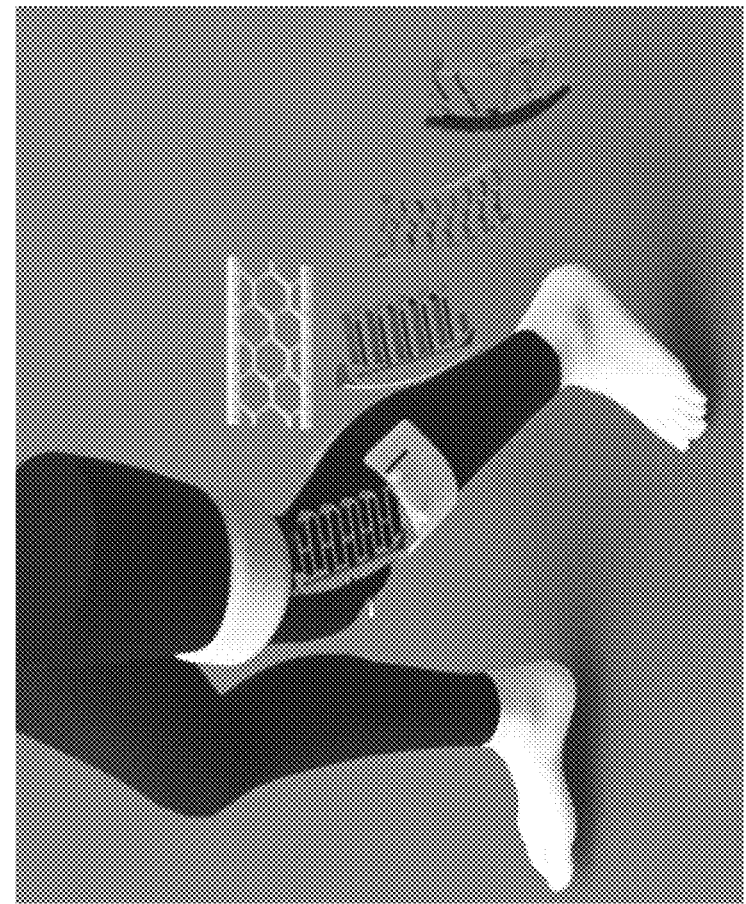
Figure 28F:
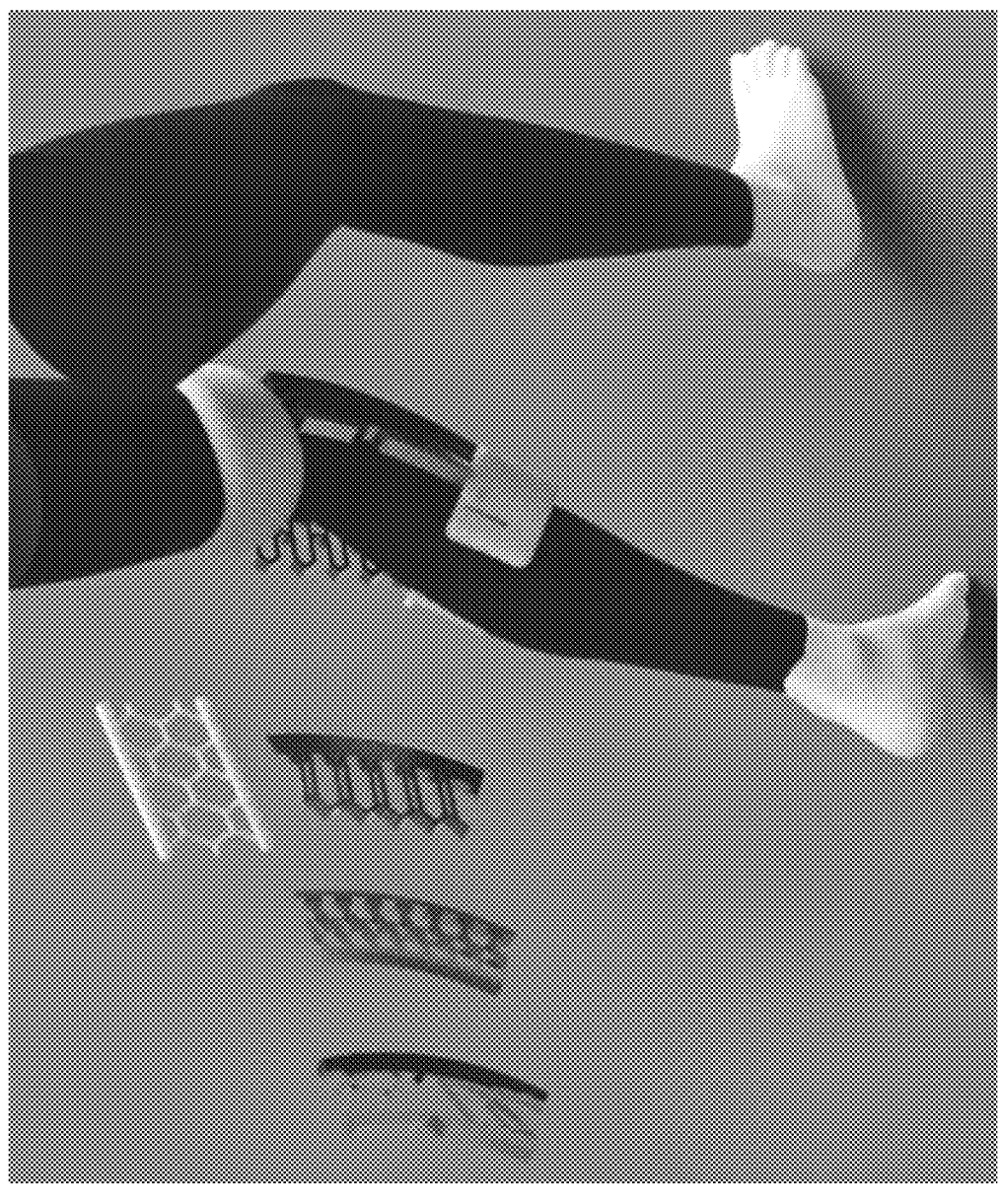
Figure 28H:
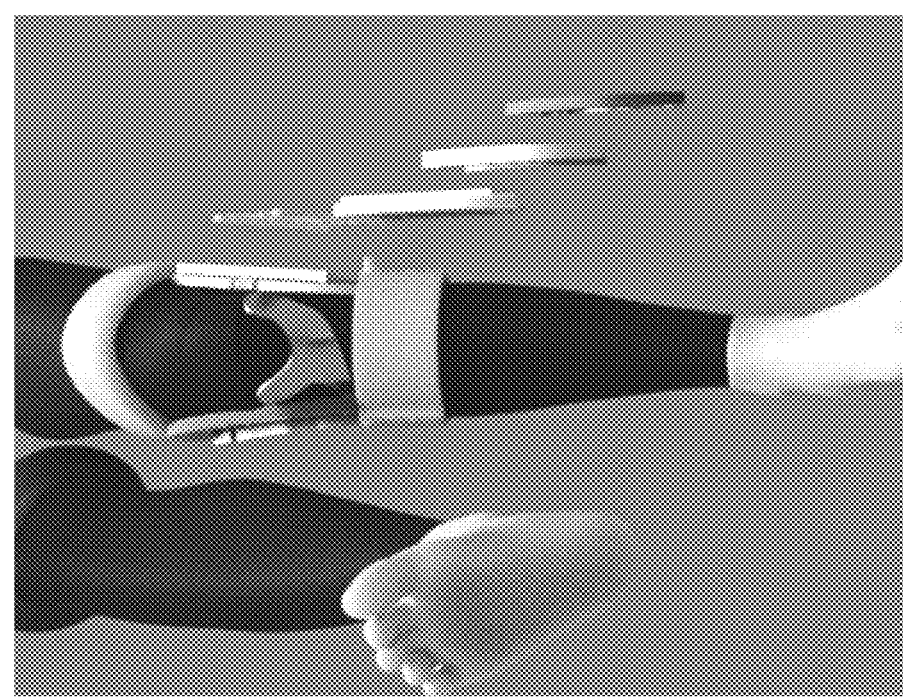
Figure 28G:
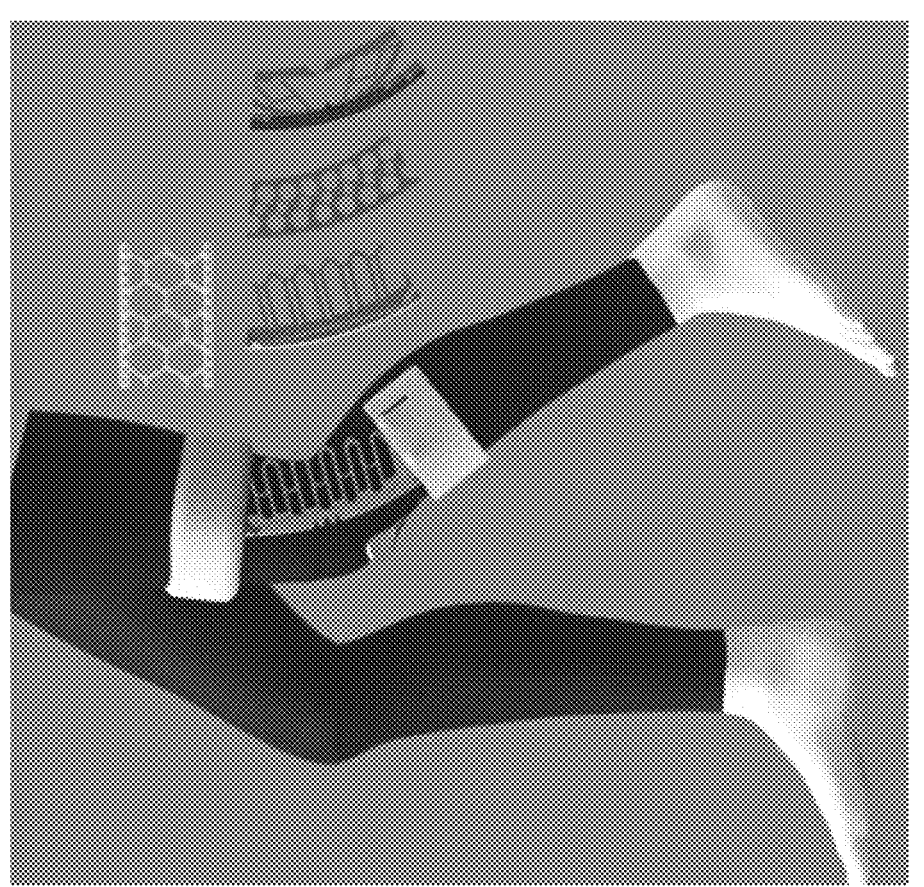
Figure 28I:
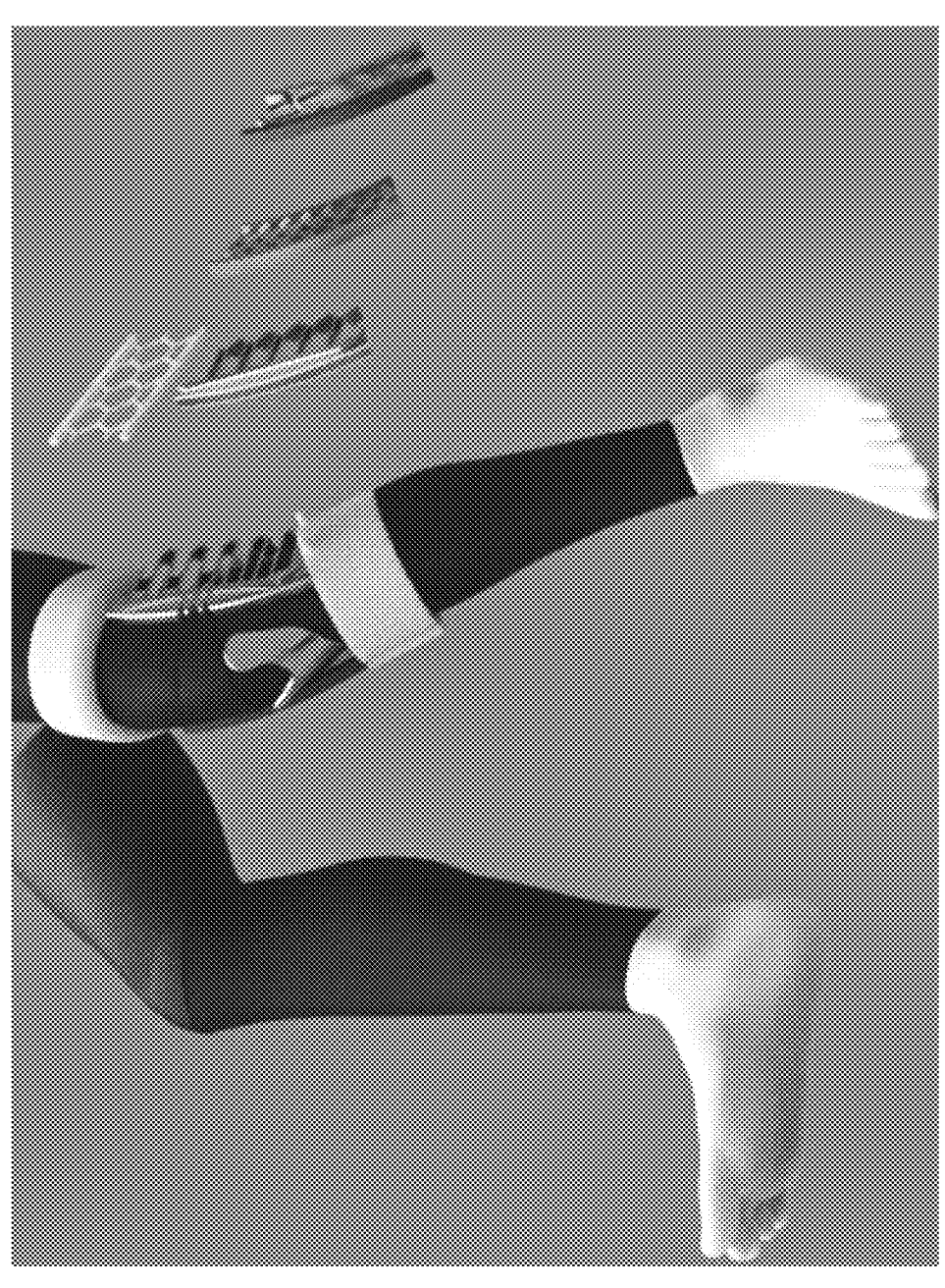
Figure 28J:
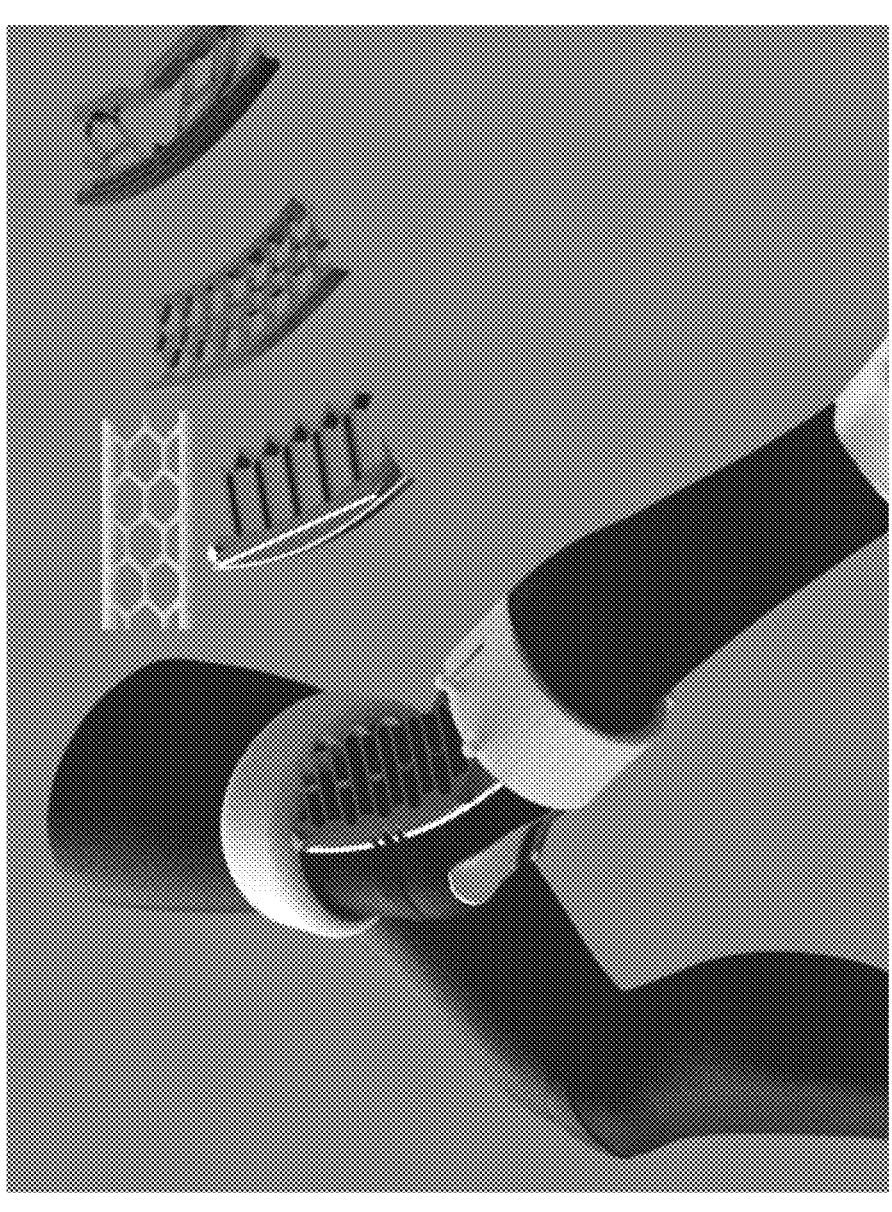
Figure 28K:
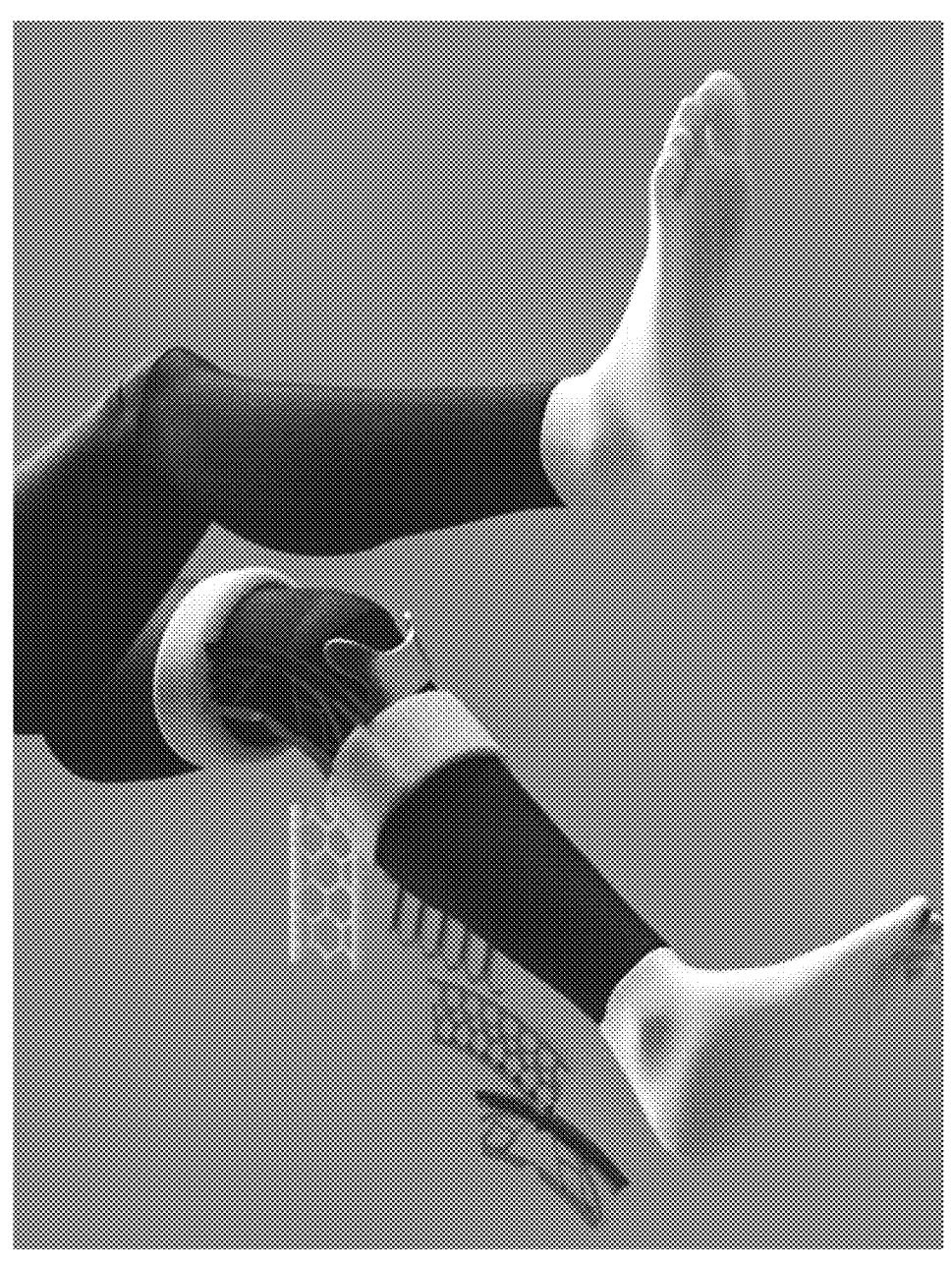
Figure 28L:
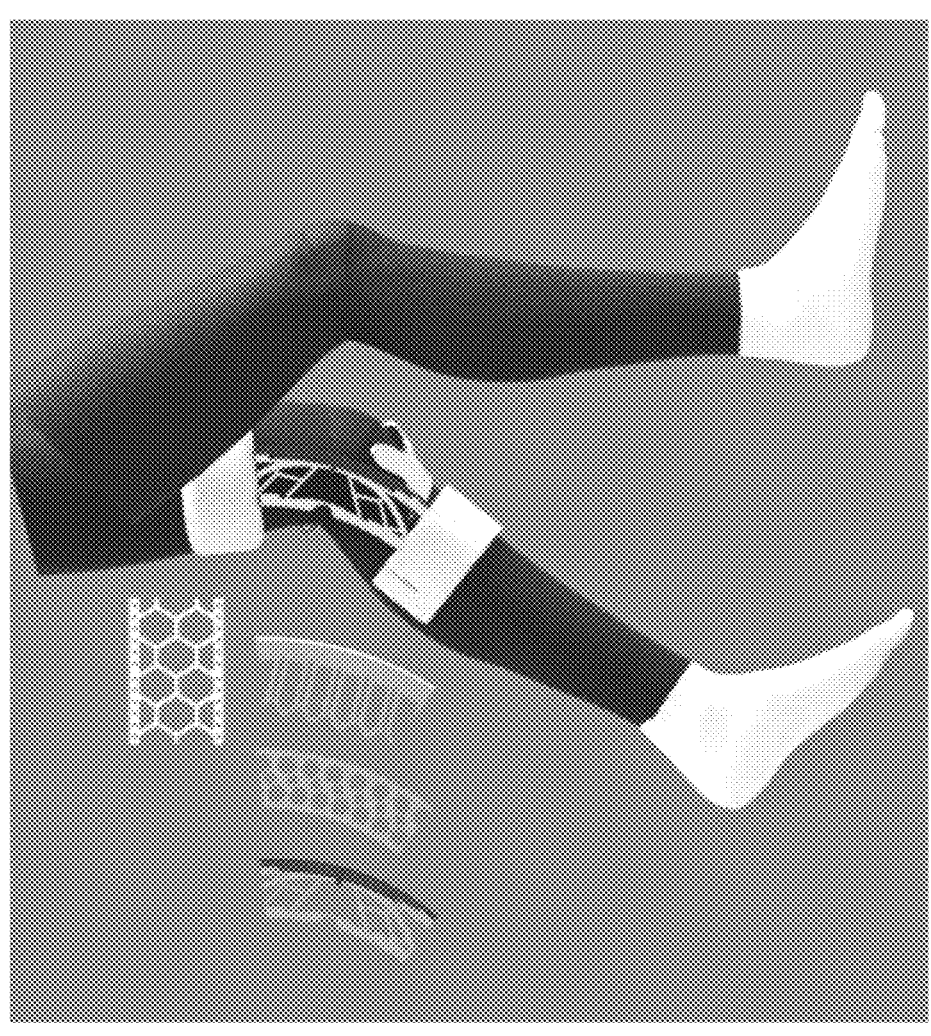

FIG. 27 illustrates an example schematic of an AI interfacing with medical professionals and an exemplary knee brace.

FIGS. 28A-28L illustrate various perspectives of an example knee brace on a patient.

DETAILED DESCRIPTION

Introduction

The product here defined is a modular knee brace system that includes a knee brace, and which may include one or more modules, where the system is portable, and allows the user to swap in and out various modules or accessories that may be used in conjunction with the knee brace. Such modules and accessories may provide for knee extension and/or immobilization when desired, application of cooling or heating, directional stability characteristics, and the like, as described herein. The knee brace is configured specifically for recovery from injury, or surgery, rather than a knee brace that may be worn while participating in athletic events, for additional knee support. In an embodiment, the knee brace does not include any mechanical arms or linkages intended to assist or aid flexion movement of the knee. That said, in some embodiments, such mechanical arms and/or linkages (e.g., rigid metal or rigid plastic linkages) could be included, if desired.

The knee brace generally includes a breathable shell layer for providing support around the knee of the user. The material of such shell layer may be breathable, increasing comfort, and user compliance to a treatment regimen. The brace may include a removable insert, which may be relatively rigid (e.g., significantly more rigid than the surrounding breathable shell), for insertion into a pocket or similar structure of the knee brace, to provide extension (e.g., terminal extension) of the knee when the insert is inserted. This may allow a resting user to periodically insert the insert while seated (e.g., with the leg elevated above the ground), resting and immobilizing the knee in a 0° "full terminal extension" position. Where the insert is selectively removable, this allows the user to remove the rigid insert, such that the user can take a break from such immobilization, and even walk around (with knee flexion) should they so choose. When immobilization is again desired, the insert may be re-inserted.

The system may further include an elevation stand, e.g., a bipod or other support that may be attachable to the knee brace, allowing the user to elevate the knee (e.g., in full terminal extension position), with the foot elevated off the ground, when desired. Such a stand may be portable, and detachable from the knee brace, allowing the user to take the stand with them, with the brace, or to leave it home or at work, etc., should they not desire to use the stand.

The system may further be optimized by including AI driven custom printed components. AI driven therapy may be incorporated by collecting patient data during patient/client intake interviews, during the exam for treatment, and/or at other times relevant to treatment. Data may be collected as part of a medical intake form during screening in the form of a check list with measurements associated with each unique patient. This feature allows for long term patient of care standard and use. Additional features will be discussed in further detail below.

Exemplary Braces and Associated Methods of Treatment

Figures 1, 2:
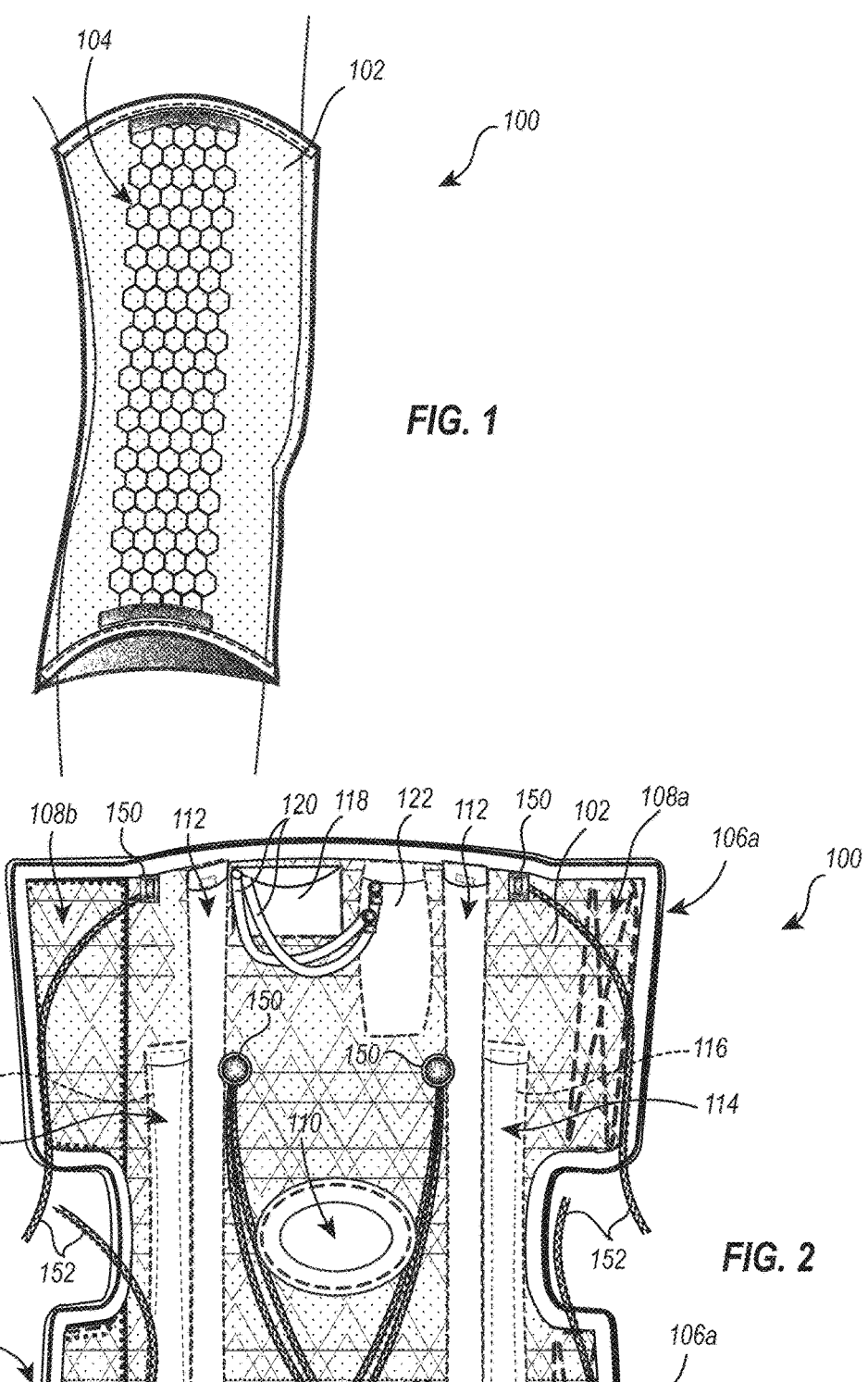
FIG. 1 shows an exemplary knee brace over the leg of a user.
FIG. 2 shows a schematic view of an exemplary knee brace, shown unfolded.

FIG. 1 illustrates an exemplary knee brace 100. The knee brace device 100 may include a breathable elastomeric, flexible shell 102. Such shell may be in the form of a mesh, or other patterned fabric or other material, as shown. The material of such a shell may be a "spandex"-like material (i.e., with elasticity), a nylon and/or cotton breathable canvas (e.g., a blend of nylon and cotton), such as the material from which Sunbrella™ is formed of, or the like. Aeroprene is another example of a material that may be suitable for use. Various suitable materials will be apparent to those of skill in the art. Such may be provided in a variety of colorful, attractive fabrics. Such may include, but are not limited to solid colors (e.g., Apple Red), inclusion of optional school logos and/or colors (e.g., licensed logo usage). Additional various exemplary colors, fabrics and/or nature-based themes may include storm grey; aquamarine blue, solid gold; maroon or burgundy; violet plum; grass green, cobalt, asphalt dark grey; or midnight black. Any conceivable color, fabric, or the like may be provided, based on its availability.

The shell may include a structure providing tensegrity. For example, materials, patterns or geometry, supporting straps, struts, or the like may be provided, e.g., woven into or otherwise provided with the breathable fabric shell 102. FIG. 1 schematically illustrates an example of such in the hexagonal mesh shown along the medial and/or lateral sides of the knee brace, at 104. While a hexagonal structure is shown, it will be appreciated that a wide variety of geometries or patterns may be appropriate, e.g., configured to provide dimensional stability in the knee brace. By dimensional stability, e.g., it is meant that the pattern or geometry may provide greater resistance to an applied force in one direction as compared to resistance in another direction. For example, the pattern (and thus brace) may accommodate greater force or movement in a compressive direction as compared to greater resistance that may be provided in another direction. Such directional differences in offered resistance may aid the knee brace in providing support against particular undesirable movements. For example, it may be desirable to resist against medial/lateral movement of the knee joint, or other movements that are not natural to the normal flexing intended to be accommodated by the knee joint.

FIG. 1 shows how such a geometry or pattern may be provided at specific portions of the knee brace shell, e.g., along the medial and/or lateral sides thereof. In another embodiment, a desired pattern or geometry providing such characteristics could be provided throughout the shell structure, where such would be desirable. In an embodiment, such a pattern or other geometry may be provided in pockets or otherwise within specific regions of the knee brace shell. Such elements may conceivably be removable, allowing a user to remove a given insert with a particular geometry or pattern, providing particular directional stability characteristics, and possibly replace it with a differently configured insert, which may provide different characteristics. In another embodiment, such geometries or patterns could be sewn into, or otherwise permanently (fixedly) integrated into the shell structure.

FIG. 2 shows knee brace 100 in an unfolded configuration. For example, in an embodiment, the brace may include VELCRO (i.e., hook and loop) fastener or other fastening mechanisms for wrapping the brace 100 around the knee and surrounding leg portions of the user, as seen in FIG. 1. FIG. 2 illustrates the presence of side flaps 106a which may be coupled to side flaps 106b, by wrapping the shell 102 around, as will be apparent from the Figures. A first portion 108a of VELCRO or other fastener is shown at side flaps 106a, while the corresponding other portion 108b of the fastener may be provided at opposite flaps 106b.

While shown in an unwrappable configuration in FIG. 2, it will be appreciated that in another embodiment, the knee brace shell 102 may be configured as a continuous wrap or loop, such that it is instead pulled up over the leg, rather than wrapped therearound, and then secured. Such a continuous (i.e., 360°) wrap may not have the illustrated VELCRO or other fasteners, instead simply relying on the elasticity of the wrap to hold it tightly in place.

Knee brace 100 is shown with an opening 110 which may be configured for placement over the patella, with the opening roughly corresponding in size and shape to the patella of the user, such that the top portion of the knee (i.e., the patella) is exposed through the opening 110 of the brace. In another embodiment, no such opening may be present.

FIG. 2 illustrates numerous various structures that may be included with the knee brace, e.g., in any combination (e.g., some may be present, others not, as desired). Pockets 112 may be provided for insertion of a hexagonal honeycomb insert (as at 104 in FIG. 1). As noted above, while FIG. 1 illustrates a hexagonal honeycomb geometry, it will be appreciated that a wide range of geometries and patterns (e.g., various polygons, or the like) may alternatively be used. Additional examples of such directional stability geometries are shown in later described Figures.

One or more pockets 114 may be provided for insertion of a knee extension insert, e.g., formed from a relatively rigid material (e.g., metal, plastic, wood, or the like) for insertion into pocket(s) 114, providing extension (e.g., terminal knee extension) to the knee when inserted therein. Such an insert 116 may be configured as a posterior extension stiffener, such that when it is inserted, it rests along the back of the knee, providing extension (e.g., full terminal extension), when inserted. Such a pocket allows such a posterior extension stiffener to be inserted at will, by the user, when forced extension of the knee is desired. The modular nature of the system allows removal of the stiffening insert, allowing the user to again flex the knee back from full terminal extension, when such is desired. The removability of the insert 116 from pocket 114 allows the user great flexibility with the knee brace, such that with the insert in place, the knee brace may serve as an immobilizer, offering full terminal knee extension (i.e., 0°). Because removal of the insert is possible, this offers the user excellent flexibility in how they use the knee brace and associated system.

FIG. 2 illustrates various other optional components that may be provided as part of the system. For example, a pump 118 may be provided. A thermal pad or heat exchanger may be provided for providing cooling and/or heating to the knee brace. By way of example, such may be as simple as providing a pocket into which a heating pad or cooling pad could be introduced (e.g., which is cooled in a freezer or heated in a microwave by the user). In other embodiments, tubing for circulating coolant or a heating fluid throughout the shell 102, or particular portions thereof may be provided, as will be described in greater detail below. Similarly, heating elements (e.g., resistive heating wires or other elements) could be provided for delivering heat through shell 102 or portions thereof. Pump 118, as well as tubing 120, and reservoir 122 (e.g., a canister) are examples of such heating or cooling components. In an embodiment, such components (e.g., pump 118, reservoir 122 or the like) may be held in or to the knee brace, e.g., in a pocket, belt, or the like, as shown in FIG. 2. In another embodiment, such modular components, which may be used, or left behind, could be housed in a backpack (FIG. 20) or the like. It will be apparent that numerous configurations are possible.

The knee brace system may optionally include an exo-skeleton structure to provide POST. Any of the geometric patterns described herein may be used for such exoskeleton support, within or about the shell of the knee brace, aiding to support the knee protected therein. The system may further include a portable elevation stand, for use in elevating the user's foot and/or lower leg (i.e., below the knee) above the ground. Such various modular components are described in the Figures that follow.

Figure 3:
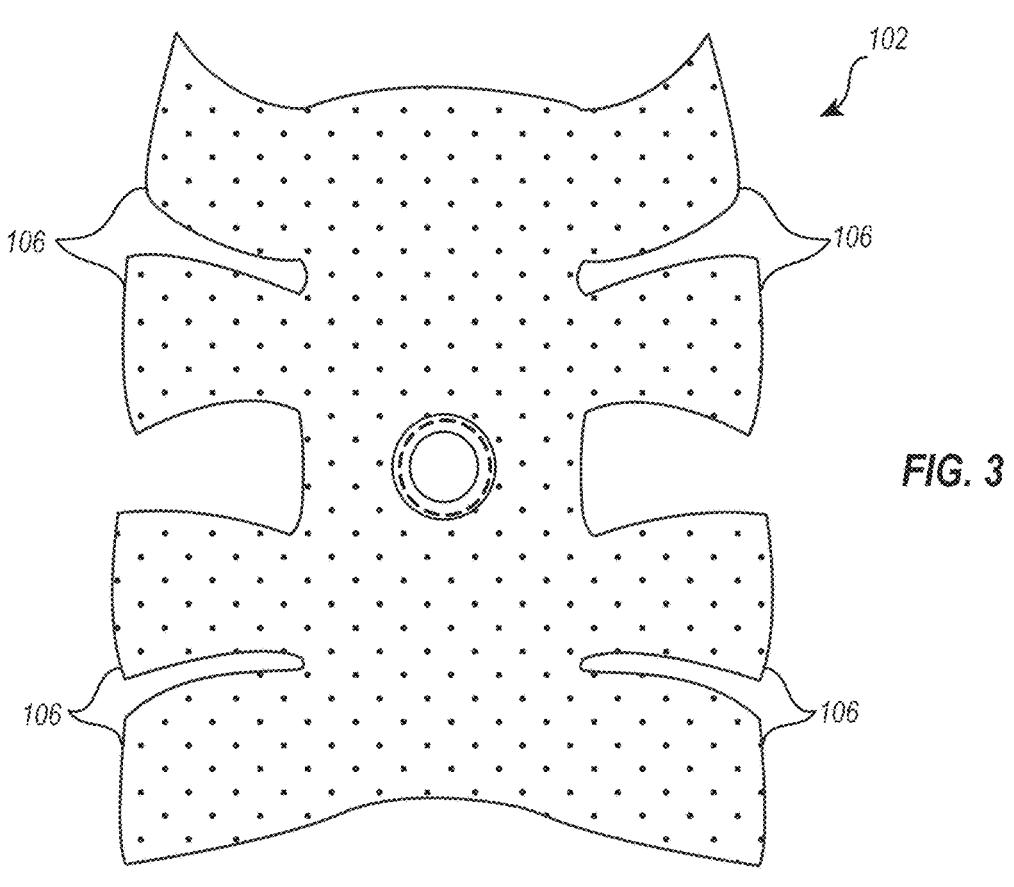
FIG. 3 shows how the breathable shell of the knee brace may include angular straps configured to be secured to one another.

Examples of the breathable shell are further shown in FIGS. 3-5B. For example, FIG. 3 shows breathable shell 102. Any fabric or other material that is breathable (e.g., with the ability to allow moisture vapor to be transmitted therethrough) may be used. The breathable shell may be produced by a tri-planar architecture and 3d printing. The breathable shell may also be produced by electrospinning or other appropriate means of manufacturing a breathable shell. By way of example, those of skill in the art will appreciate that various standardized tests may be used to determine breathability, as described in the Wikipedia entry on "Breathability", herein incorporated by reference. Examples of materials and associated measurements are described therein, a summary of which is shown below in Table 1.

TABLE 1

| Exemplary Materials | RET (Hohenstein Test) | B-1 (Inverted Cup Test) | A-1 (Upright Cup test) |
|---|---|---|---|
| Non-coated fabrics | 2-4 | 25000 ++ | N/A |
| MemBrain, Gore-Tex Pro 2L-3L | 4-6 | 25000+ | 4000-8000 |
| Gore-Tex PacLite, Performance 2L, Entrant HB, PreCip Plus | 6-8 | 15000+ | 8000-15000 |
| Gore-Tex Performance 3L, PreCip, MemBrain 10, Entrant GII | 7-10 | 10000-15000 | 5000-12000 |
| Windstopper Softshell, Low end Entrant, most Softshells with film | 8-13 | 6000-10000 | N/A |

RET values do not typically have units. Units for B-1 and A-1 values have units of g/m2/day. RET is a measurement of the resistance to evaporative heat loss. The lower the RET value, the less resistance to moisture transfer and therefore higher breathability. Higher values for B-1 and A-1 tests correlate to higher breathability. By way of example, the selected breathable fabric or other breathable material may have an RET value of less than 20, less than 15, less than 13, less than 10, or less than 6. B-1 values may be greater than 10000 g/m2/day, greater than 15000 g/m2/day, or greater than 20000 g/m2/day. A-1 values may be greater than 4000 g/m2/day, greater than 6000 g/m2/day, greater than 8000 g/m2/day, or greater than 9000 g/m2/day.

Figure 4:
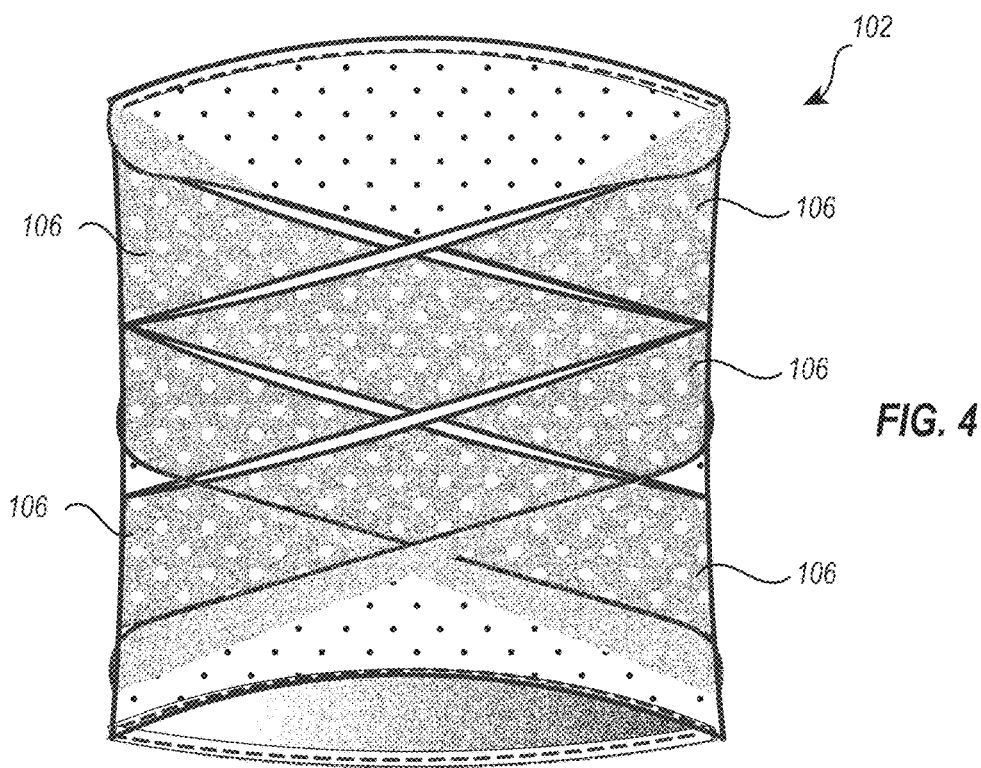
FIG. 4 shows another embodiment in which the shell of the knee brace may include a criss-cross weave of straps.

As shown in FIG. 2, the breathable shell may include various pockets and/or anchoring places (e.g., for the various inserts, for the pump, for the canister, etc.). The configuration shown in FIG. 3 illustrates a plurality of straps or flaps 106 which may be attached to one another, e.g., as described above in the description of flaps 106a, 106b of FIG. 2. FIG. 4 illustrates another configuration showing a criss-cross weave configuration for such straps or flaps that may be employed in the knee brace. Such criss-cross, upwardly oriented straps may promote circulation, edema management, and improved, intelligent support to the underlying structures of the user surrounding the knee. Such interweave configurations may improve joint protection and POST characteristics. As described above, the material weave could include any of various geometrical designs or configurations (e.g., honeycomb seen at 104 in FIG. 1), e.g., to provide directional stability.

The breathable shell may be impregnated with flexible or rigid binding materials, e.g., such as, but not limited to adhesives, polymers (e.g., silicone, latex, polyethylene, polypropylene, or other polyolefin or other polymeric material). Such impregnating or coating materials may serve to hold fibers of the breathable shell material together in desired configurations, e.g., to provide directional stability. In other words, such coatings or impregnating materials may be provided in a desired pattern to provide directional stability (i.e., to provide greater resistance to movement in one direction as compared to another direction). Such impregnating or coating materials may be applied via any suitable printing method, silk screening methods, or the like to apply such materials to precise locations, as needed to achieve the desired directional stability characteristics. Where such materials may decrease breathability of the underlying fabric material, care can be taken to ensure that such materials do not fully coat the entire fabric surface, so as to ensure maintenance of sufficient breathability.

In an embodiment, the breathable shell (e.g., through structures such as those described herein) may provide a positive tension mechanism for extension assist. For example, directional stability built into the shell may create a biasing for the user towards a knee extension movement, facilitating exercise of the user's muscles and other anatomical structures as the user moves the knee in a flexion movement, so as to overcome the bias imposed by the positive tension mechanism (e.g., directional stability) built into the shell. While described in the context of a bias towards an extension movement, it will be appreciated that the shell or other device structure may provide such directional stability directed to other movements as well (e.g., to provide bias against knee extension, or torsion, or lateral movement, etc.).

FIGS. 5A-5B illustrate additional breathable shell configurations 102. For example, as shown in FIG. 5B, the breathable shell 102 may include a particular weave such as an "edema cloth", configured to reduce risk of edema to the user. Such an edema cloth weave and/or material may be incorporated as a layer within the breathable shell, or the entire shell may be formed from such a material. For example, in an embodiment, the breathable shell may include a layer of breathable fabric material as seen in FIG. 5A, as well as a layer of edema cloth as shown in FIG. 5B (e.g., stacked one over the other). Such edema cloth materials are available from various commercial sources, which will be apparent to those of skill in the art. It will be apparent that any of the various structures or layers shown herein may be stacked or otherwise provided in combination one with another.

FIG. 5C shows how the shell 102 may include a "circulation piece" for facilitating flow of coolant (or heat) through the shell. The circulation piece or layer 124 illustrates one possible serpentine circulation pathway that may be provided in the knee brace device (e.g., within the shell thereof). In an embodiment, such circulation tubing may be of a flaccid, lay-flat configuration, such that when no coolant (or heating fluid) is contained in or flowing therethrough, the tubing lays substantially flat, e.g., analogous to the packaging of an OTTER-POP or similar freezer pops. When the coolant or heating fluid is introduced into such circulation tubing (and pressurized to some degree), the initially flat laying tubing protrudes upwardly as it is filled, and the coolant or other fluid flows therethrough, e.g., under pressure provided by pump 118. Such lay-flat tubing may aid in ensuring compactness of the overall knee brace and the shell. Such tubing may include a port to which a pump and/or reservoir/canister can be connected, providing the fluid to be circulated therethrough. FIGS. 2 and 5D illustrate such connective tubing 120 on outer cover 100' that may allow circulation of such coolant or other fluid (e.g., heating fluid) from the reservoir (e.g., a canister) 122 through pump 118 (using tubing 120), into such circulation tubing 126. While a serpentine arrangement for such lay-flat tubing is shown, it will be appreciated that numerous other configurations are of course possible.

Figures 6A, 6B, 6C, 6D:
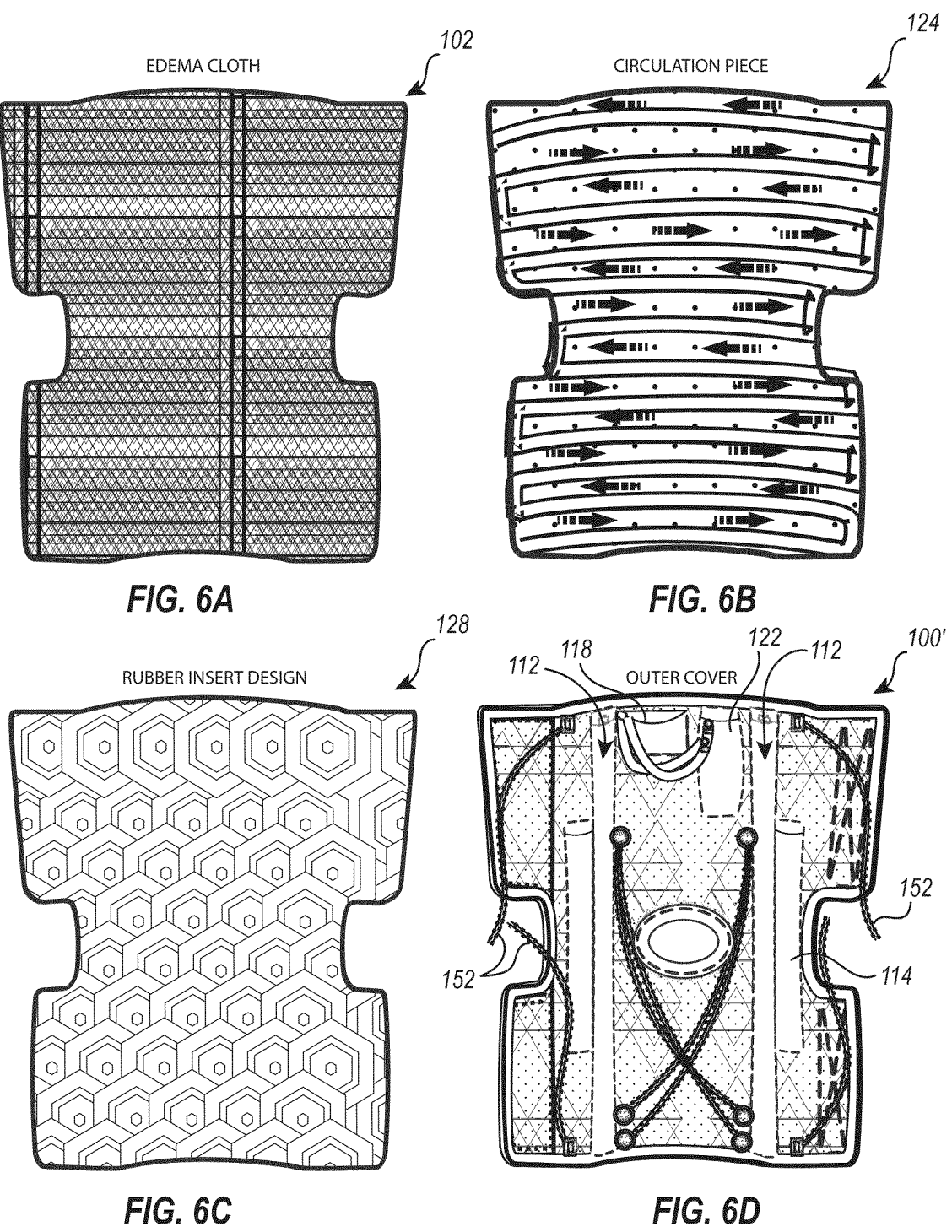
FIGS. 6A-6D show another exemplary configuration, showing an edema cloth layer, a circulation piece, a rubber or other elastomeric insert design, and an outer cover, respectively.

FIGS. 6A-6D illustrate a similar "stack" as that of FIGS. 5A-5D, illustrating how various layers or other structures may be provided therein. The layer seen in FIG. 6A may be an edema cloth layer similar to that seen in FIG. 5B. The circulation piece or structure seen in FIG. 6B is similar to that seen in FIG. 5C. FIG. 6C specifically illustrates a rubber or other elastomeric insert configuration 128 that may be included in the stack. FIG. 6D shows the outer cover layer 100', which is how the stack may appear, with the various layers of FIGS. 6A-6C disposed thereunder, stacked one over the other.

The various layers shown in FIGS. 5A-5D and 6A-6D illustrate one aspect of the modularity of the system. For example, the inner-most layer may be an edema layer, to control and minimize risk of edema, followed by a breathable layer, then any of the various other illustrated layers (e.g., elastomeric pattern layers, circulation layers, etc). An exoskeleton layer, such as that shown in FIG. 17 may be present, e.g., typically as one of the more outer-most layers (if not the outer-most layer). For example, an exemplary layer stack may include an edema control layer, a breathable fabric layer, a circulation layer, and an exoskeleton. Any of such layers may be separate or separable from the other layers, allowing the user to mix and match, various components or module selections, as desired. In an embodiment, at least some such layers could be integrated together into one piece (i.e., not separable from one another), e.g., analogous to how a tire has a number of layers fused together. For example, the edema control layer and the breathable fabric layer could be integrated together, an exoskeleton structure providing directional stability could be sewn, strapped, or otherwise attachable to the outer cover layer, or the like. It will be apparent that numerous such possibilities are possible.

Figures 10, 11A, 11B, 11C, 12:
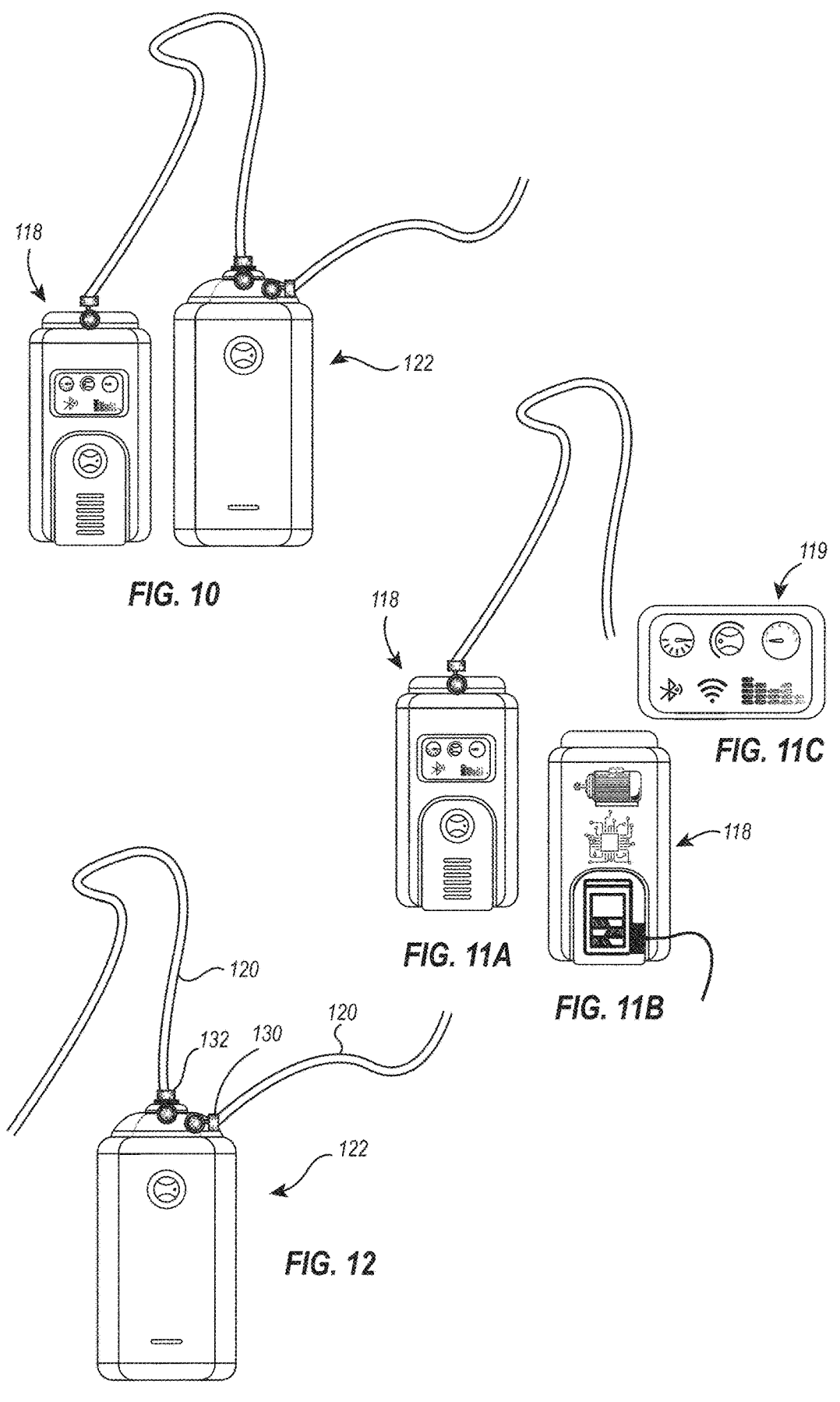
FIG. 10 schematically shows a pump and associated reservoir (e.g., canister) that may be used to circulate coolant (or a heating fluid) through the knee brace.
FIGS. 11A-11C schematically show the pump of FIG. 10.
FIG. 12 schematically shows the reservoir of FIG. 10.

The pump 118 and canister reservoir 122 seen in FIGS. 2 and 6D are also shown in further detail in FIGS. 10-12. FIG. 11A shows the front of pump 118, while FIG. 11B shows the rear of pump 118. FIG. 11C illustrates controls 119 of pump 118. Any of various suitable pump configurations may be suitable for use. Non-limiting examples include a peristaltic pump (e.g., linear or rotary), an empeller pump, a syringe pump, a piston pump, or the like. Various possibilities will be apparent to those of skill in the art. As shown in FIG. 2, the pump may preferably be relatively small, e.g., so as to be able to fit within the pocket of the shell 102, or otherwise be anchored or tethered to the shell (e.g., clipped onto a belt, etc.). In addition to being relatively small, the pump may also preferably be light-weight, so as not to significantly affect the gait of the user, or to otherwise be cumbersome. By way of example, the pump may have a maximum length, width, or depth dimension that does not exceed 8 inches, 6 inches, or 4 inches on any side. The pump may have a weight that does not exceed 3 lbs, 2 lbs, 1 lb, 12 oz, or 8 oz. The pump may be such so as to not significantly affect ambulation (i.e., the ability to walk about from one place to another) with the pump anchored to the worn knee brace, or stored in a backpack (FIG. 20).

The pump may be battery powered (e.g., AA, AAA, or 9V batteries, for example). The pump may be rechargeable, and may run for at least 2 hours, at least 3 hours, or at least 4 hours on a single charge. The pump may also run off wall socket power (e.g., corded). The pump may have Bluetooth or other wireless connectivity, e.g., being internet or other data transmission capable. Such capability may allow a user to control the pump from an app, e.g., on the user's smartphone. The pump may be programmable to perform under various regimes, e.g., to circulate coolant or heat for a particular number of minutes, to select start and stop times, capable of variable speeds, capable of pulsing, (e.g., pulsing directional gradient to move fluids, perform massage, or the like), capable of flow reversal, capable of measuring coolant/heating fluid temperature and the like. An exemplary cycle may include some period of time on (e.g., 20 minutes), followed by turning off, or followed by a rest period, after which pumping resumes, etc. Another exemplary pumping regime may include pumping for some number of minutes (e.g., 20 min) followed by a rest period (e.g., 15 minutes), which is repeated for some number of cycles (e.g., 10 cycles). Pump times may vary from 1 to 30, 2 to 20, or 5 to 20 minutes. Rest times may be similar. Number of cycles may range from 1 to 100, 2 to 50, or 3 to 20, by way of example. It will be apparent that a wide variety of regimes may be possible.

In addition to or alternative to providing cooling, the system may be configured to provide heating. Heating or cooling may be provided by a thermal pad with heat exchanger tubing, other coils, e.g., resistive heating element(s), or the like. The thermal heating/cooling system may be conformal to the knee, and may particularly deliver cooling or heating to the lower thigh and/or upper hip area of the user. Soft, thin material may be provided against the skin of the user for increased comfort and moisture wicking capability. The coil design (whether for heat or cooling) may incorporate different coil diameters or sizing, and or varying concentration of such coils to concentrate delivery of thermal therapy to specific key areas, such as posterior, medial, and/or lateral areas of the device and the user's knee area. The thermal pad or module may include connectors to connect to other third party pumps or circulators (other than that provided with the knee brace supplier). As described above, such coils may be configured as flaccid, lay-flat tubing (e.g., tubing 126 as in FIG. 5C). Such flaccid lay-flat "coils" could be incorporated into the breathable shell structure, or an adjacent layer, as is apparent from FIGS. 5A-5D, showing various exemplary layers that may go into the device.

Canister reservoir 122 is also seen in FIG. 2, and shown separately in FIG. 12. Canister 122 (also referred to interchangeably as a reservoir) may be fabricated using any suitable thermal (e.g., insulated) conservation design, e.g., found in many off the shelf insulated water bottles or "thermos" type containers (e.g., for keeping coffee, tea, or other food or beverage warm or cold). As seen in FIG. 12, the canister or other reservoir may include in and out ports 130, 132, respectively for facilitating circulation of coolant or heating fluid from the reservoir, to pump 118, through coils 126, and back into reservoir 122, for example. Reservoir 122 may be filled with cold (e.g., icy) water or other cold or icy fluid. Where the reservoir is used to provide circulation of heat, the reservoir could alternatively be filled with hot water or other hot fluid. If both heating and cooling are provided, two separate reservoirs could be provided, a single canister with separate reservoirs for hot and cold, or various other configurations could be provided. For example, cooling could be provided by circulating chilled fluid (e.g., ice water or other) from reservoir 122, while heating could be provided by electrical resistive heating coils that also run through shell 102, in a desired serpentine or other pattern, analogous to coils 126 seen in FIG. 5C or 6B.

In an embodiment, the thermal fluid used for circulating through such coils 126 may include components other than or in addition to water, e.g., providing enhanced cooling or heating properties. For example, such composition may include glycerin or other components suitable for such, as will be appreciated by those of skill in the art. By way of example, chillable/freezable fluids such as those used in various freezer packs could be used. The reservoir or canister could be provided in two or more sizes, e.g., a relatively small size for ambulatory use, and a larger size for stationary use. For example, where the user intends to remain stationary, a larger, higher capacity reservoir or canister may be provided for use, providing longer cooling or heating times before requiring reheating or recooling or replacement of the fluid in the reservoir. In an embodiment, two such different sizes could be made available for use with the knee Brace system. More than two such sizes of reservoirs could of course be provided.

The smaller ambulatory size reservoir may be sized and shaped so as to fit within the pocket or other anchoring point provided in shell 102, as seen in FIG. 2. Such reservoir 122 would preferably be sufficiently small so as to be non-cumbersome, and so as not to impede the user's gait. Such a configuration in which the reservoir may be attached to shell 102 advantageously allows the user to be hands free during operation of the system, e.g., receiving cooling or heating, without having to hold reservoir 122 (or pump 118), while being able to walk around, from place to place (i.e., ambulation). While shown in FIG. 2 attached to shell 102, it will be appreciated that other similar solutions could be provided that provide similar benefits, e.g., by anchoring such reservoir and/or pump 118 on a belt or in a backpack (FIG. 20). The size and weight dimensions of the reservoir may be similar to those described herein relative to the pump, whether the reservoir is empty or loaded (e.g., under 3 lbs, 2 lbs, or 1 lb, etc.).

Figures 7, 8, 9A, 9B:
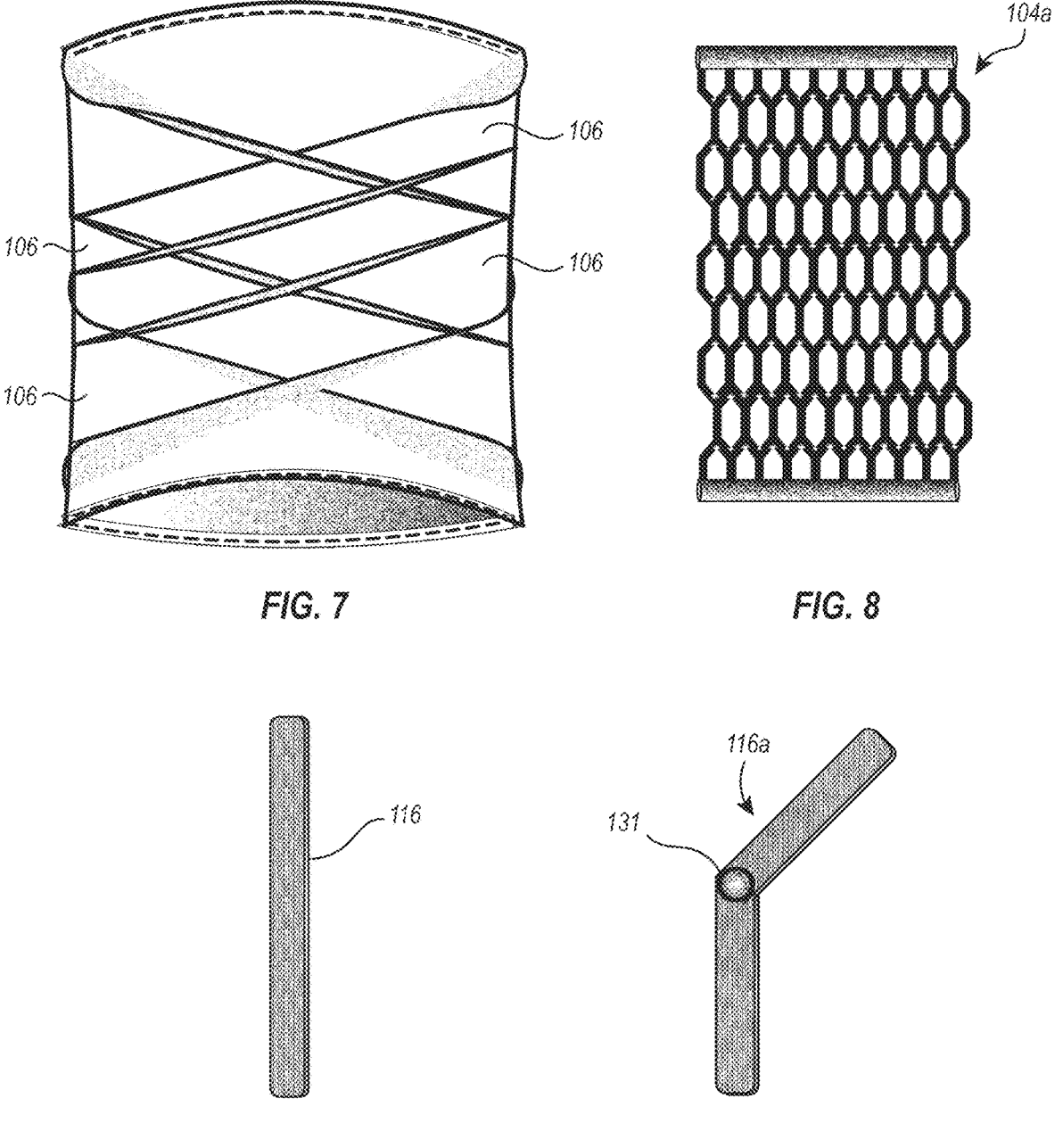
FIG. 7 shows a criss-cross weave of straps similar to that of FIG. 4, which may provide tensegrity in addition to breathability.
FIG. 8 shows an exemplary geometric design (e.g., a honeycomb) for a medial/lateral stiffener that may be provided along the medial and/or lateral portion of the knee brace.
FIGS. 9A-9B schematically show exemplary posterior extension stiffeners or inserts. The illustrated hinge may selectively or fixedly allow for 0° full terminal extension, 10° flexion, or 20° flexion, for example.

As shown in FIG. 2, the system may include removable components for providing temporary stiffness or support, e.g., such as the rigid insert(s) 116 insertable into posterior pocket(s) 114. Examples of such stiffener inserts are shown in FIGS. 9A-9B. Insert 116 seen in FIG. 9A may be straight (i.e., 180°), without any joint provided therein. FIG. 9B illustrates another insert 116a which may be similarly configured, but which may provide a joint 131 provided therein (e.g., at the center). Such a joint may be capable of being set to a fixed angle, e.g., allowing insertion into pocket 114 in a manner that would ensure flexion of the knee to a particular angle, other than the 0° full terminal extension position that may be provided by insert 116 of FIG. 9A. In an embodiment, such a joint 131 could be configured as a stop, e.g., allowing flexion of the user's knee up to a certain angle, at which stop angle no further flexion or extension of the knee would be possible. By way of example, such hinge may provide for an angle, that may be selectable by the user, e.g., of 10°, 20°, 30° or the like from full terminal extension. It will be apparent to those of skill in the art that numerous possibilities are within the scope of the present disclosure.

In any case, such inserts (e.g., 116, 116*a*) may provide for a desired knee extension (e.g., particularly a 0° full terminal extension position), may fit into pocket 114, so as to position the insert along the posterior back side of the knee during use. Such inserts could be fabricated from any suitable relatively rigid material. For example, various materials having greater rigidity than the shell layer 102, such as metal, rigid plastics (e.g., PVC, HDPE, polycarbonate) wood (e.g., bamboo) or other suitable rigid materials may be used. The foregoing are merely non-limiting examples. Numerous others will be apparent to those of skill in the art.

Various such inserts may provide directional stability. For example, an insert corresponding to geometry 104 may provide directional stability, and may be insertable into pockets 112 (see FIG. 2), e.g., along the medial and/or lateral sides of the device to provide such directional stability at such locations. Such directional stability geometric structures may be included in a removable insert, provided in an exoskeleton that may be attached to or otherwise integrated into the shell, or otherwise.

For example, an exoskeleton structure may be provided for providing POST. Such structure(s) may provide joint protection for medial, lateral, anterior, and/or posterior movements or regions, in flexion, torsion, or the like. Such structures may provide tensegrity by employing particular geometric designs to guide the knee in its natural position and to mimic muscles and tendons as they provide flexion, extension, and stabilizing movements. Exemplary geometric designs include, but are not limited to a wide variety of possible polygonal configurations, such as a honeycomb (e.g., see 104 of FIG. 1), matrices of other polygons, such as pentagons, hexagons, or other polygonal or other shapes. Different polygonal or other shapes could be mixed in a single geometry, e.g., analogous to the user of both hexagons and pentagons in the configuration of a soccer ball, so as to provide a desired geometric pattern or structure, configured to provide the desired tensegrity and/or directional stability characteristics. FIG. 8 illustrates one example of such a possible exoskeleton or directional stability geometry, 104*a*. Various additional examples are shown and described in further detail in FIGS. 13A-15E. The illustrated examples are merely exemplary, and it will be appreciated that numerous other possibilities exist.

Figures 13A, 13B, 13C:
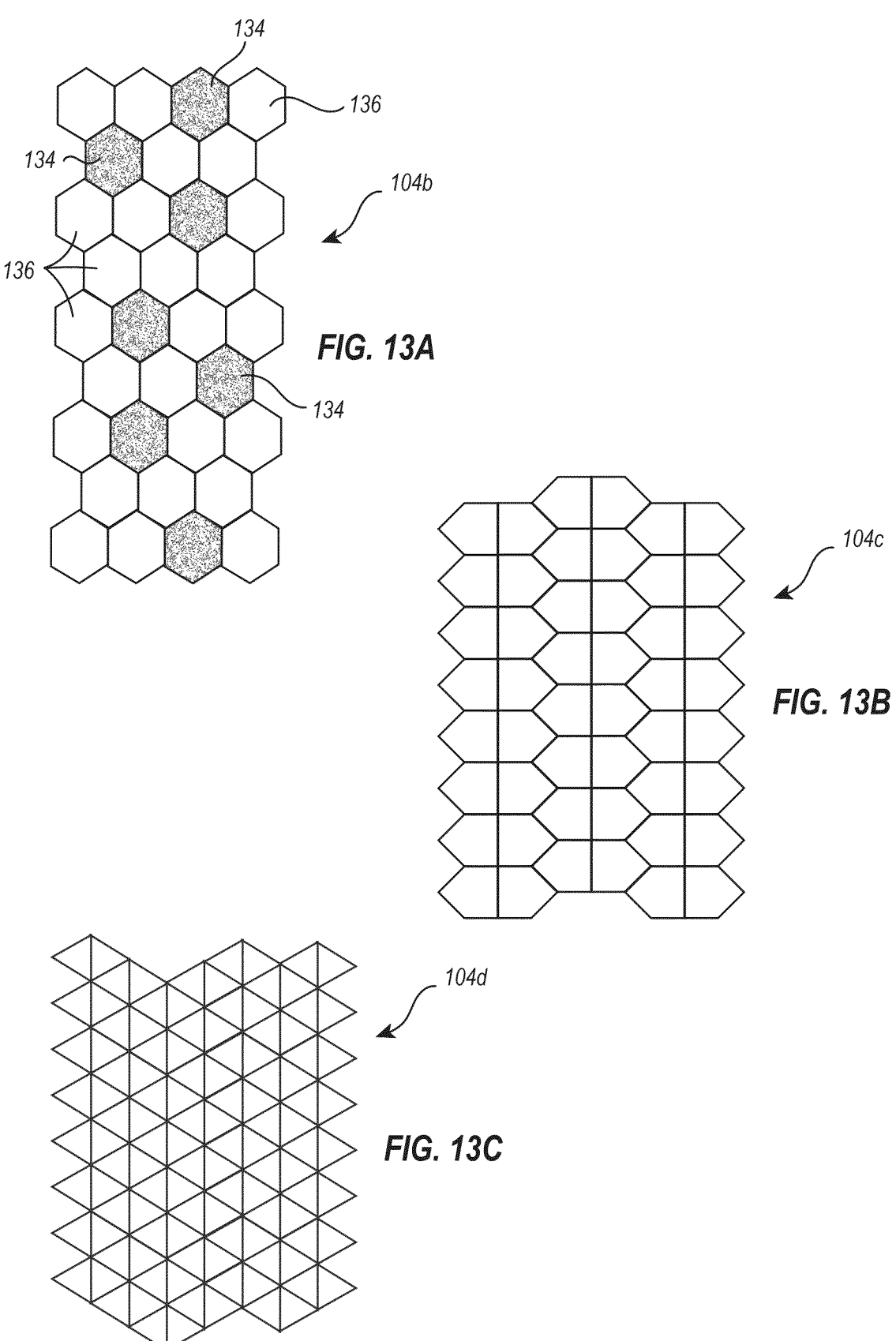
FIG. 13A shows a hexagonal geometric design that may be provided in the knee brace (e.g., for medial/lateral support).
FIG. 13B shows a pentagonal geometric design that may be provided in the knee brace (e.g., for medial/lateral support).
FIG. 13C shows a triangular geometric design that may be provided in the knee brace (e.g., for medial/lateral support).

FIG. 13A illustrates a configuration 104*b* which is similar to the honeycomb of hexagonal structures seen in FIG. 1, but in which various hexagons 134 are differently configured from adjacent hexagons 136. For example, hexagons 134 could be relatively more rigid than those of 136, or vice versa. Such variation in the matrix of hexagonal or other polymeric shapes would provide specific stability and support characteristics that could be configured to mimic the support and protection offered by natural muscle, tendon and ligament anatomical structures surrounding the knee.

Another exemplary geometry is shown in FIG. 13B, designated as 104*c*. Such a matrix or array is shown as an interlocking arrangement of pentagons, or as oblong hexagons divided down the center of their oblong (i.e., longitudinal) axis. FIG. 13C illustrates another possible geometry provided as an array or matrix of triangular shapes, designated by 104*d*.

Figure 14A:
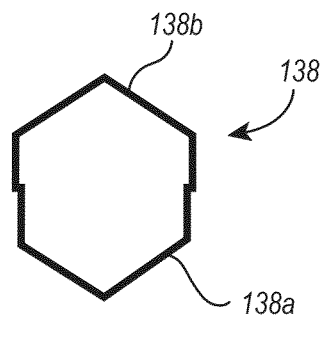
FIG. 14A schematically illustrates a geometric design for providing dimensional stability which includes a detached leg.
Figure 14B:
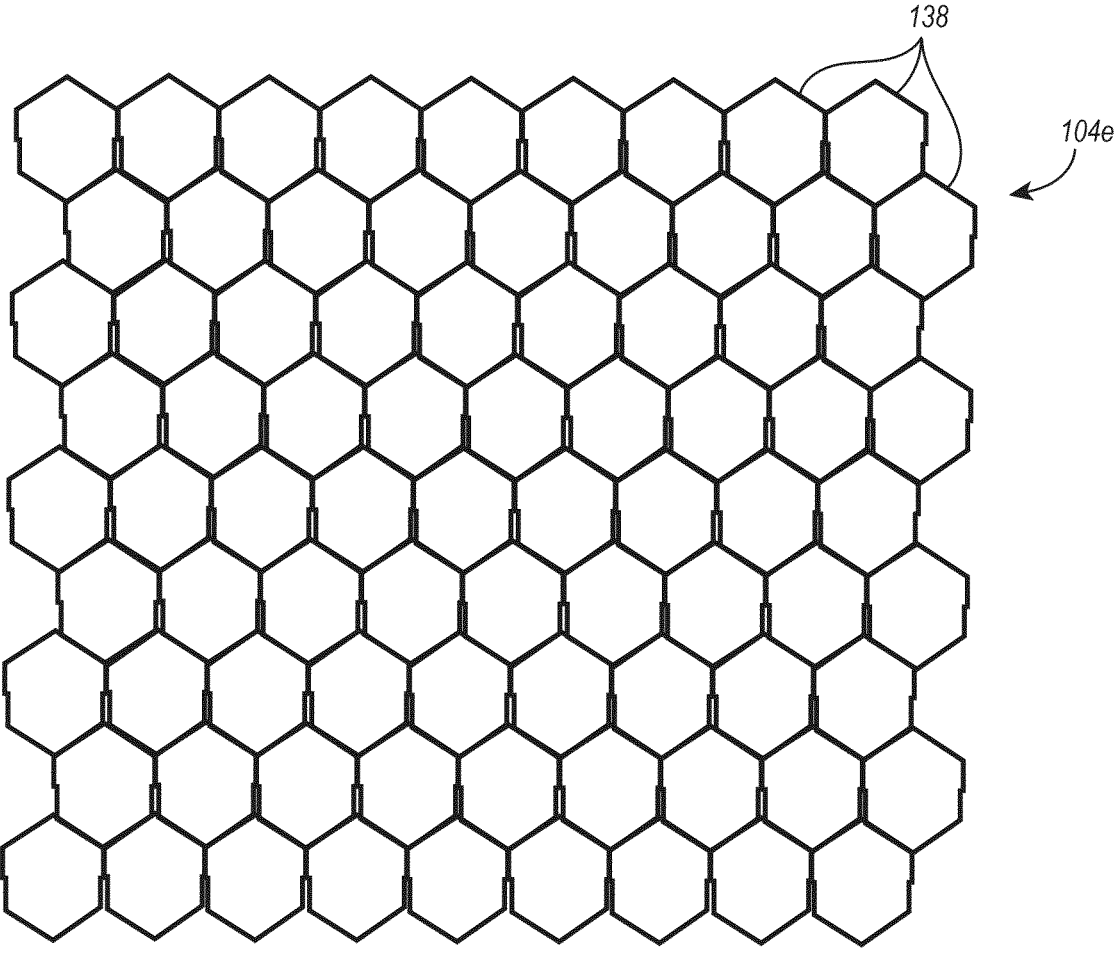
FIG. 14B schematically illustrates a geometric design formed from an array of the configuration seen in FIG. 14A, for providing dimensional stability in the knee brace, (e.g., for medial/lateral support).

FIGS. 14A and 14B illustrate another configuration which may provide directional stability by being fixed at some points of the hexagon or other polygon, while being unfixed at other points, allowing some movement or flexing in particular direction(s), while remaining more rigid in other directions. For example, the hexagon 138 seen in FIG. 14A is shown as two half-hexagons, where one half (e.g., lower half 138*a*) is able to slide within the other half (e.g., upper half 138*b*). This allows portion 138*a* to slide vertically in and out relative to portion 138*b*. It will be apparent that movement in other directions (e.g., horizontally) is not possible, but that the two portions are fixed relative to one another relative to those directions. FIG. 14B illustrates an array or matrix that could be formed from such structures, designated 104*e*. Such an arrangement would allow compression movements, collapsing the various polygons 138 vertically, where the matrix or array 104*e* were placed under compression, although no such compressive movement would be possible in the horizontal direction. It will be apparent how such a structure could be used to provide directional stability in an insert, an exoskeleton, or other structure provided as part of the shell 102 or other structure of the present knee brace. The structure shown in FIGS. 14A-14B is merely exemplary, and it will be appreciated that other structures could similarly be provided that would be configured to provide directional stability, where geometry is fixed at certain points and in certain directions, but unfixed, allowing some movement, at other points and in other directions. Such geometries could be used to allow various desired knee movements (e.g., flexion, extension, etc.), while resisting other undesired (e.g., prone to reinjury) knee movements, such as torsion of the knee, or medial or lateral movement of the knee.

FIGS. 14A-15E illustrate various other geometries that may provide similar directional stability characteristics, e.g., based on living hinge structures. For example, FIG. 15A illustrates an elongated hexagonal geometry 140, oriented vertically, which includes a thinned living hinge region 142 at the upper and lower connection points of the legs making up such a hexagon. As represented by FIG. 15C, such living hinge structures 142 may facilitate bending or flexing adjacent such points 142, while the remaining connections of the various legs of such polygonal structure are more rigid and fixed, so as to provide little if any flexibility, by comparison. This feature allows for the existence of living breaks (e.g., living hinges) where the brace has thinned and/or broken geometric structures in some areas of an otherwise closed geometric structure. In therapy, this feature may be crucial to provide appropriate stability in specific areas and a range of mobility in other areas based on the treatment regime. FIG. 15B illustrates the same array as that seen in FIG. 8, which may be made up of an array of such interlocking living hinge polygonal structures. Such an array will provide directional stability characteristics, allowing flexing or bending movements about thinned living hinge structures 142, while resisting movements about the other thicker, more rigid connections of the legs making up each polygon 140 of the array 104*a*.

In some embodiments the living hinge may also be referred to as a compliant mechanism. The living hinge allows for increased degrees of freedom in the three main planes of motion relating to the knee: the frontal plane, the sagittal plane, and the transverse plane. These three planes of motion allow for movement in the knee, such as arthrokinematics and osteokinematics. In some embodiments, the living hinge may be configured to allow movement in fewer than three planes or more than three planes.

FIGS. 15D-15E illustrate another configuration that may provide similar dimensional stability results. FIG. 15D shows a polygonal geometry 144, where the legs (or "pods") 146 are connected to one another through thinned living hinge regions 148. Relatively thick pods 146 will exhibit relatively little flexing or bending within themselves, but relatively thin living hinges 148 which interconnect adjacent pods 146 will be capable of significant flexing and bending, due to their thinness. FIG. 15E illustrates an example of an array or matrix 104*f* that could be formed from such geometric structures 144, so as to provide the desired directional stability. Again, desired directional stability configurations may allow for desired knee movements, while resisting others (e.g., knee torsion).

Any desired living hinge arrangement may provide desired, different flexibility, allowing flexure or tension in a desired precise direction, while limiting or resisting similar movement in other directions. Various materials could be used for such structures, e.g., including but not limited to PVC, polyethylene, polypropylene, thermoplastic elastomers, elastomeric silicone, etc. Otherwise rigid materials such as PVC, polyethylene, and polypropylene may provide rigidity in regions and movement directions other than where thinned in a living hinge structure, where because of the thinness of the material, flexibility and bending becomes possible in that limited direction (e.g., bending transverse to the thinned cross-section).

Such geometries may be incorporated into inserts, (e.g., for insertion into pockets, such as pocket(s) 112), or provided elsewhere or otherwise within the shell or other portions of the knee brace. For example, such geometries could be sewn into or otherwise integrated into the shell, as any of various layers (e.g., see FIG. 5A-5D, or 6A-6D, or the like).

Returning to FIG. 2, attachment points 150 may be provided for attachment of bungees, elastic ribbon, or other elastomeric elongate linkage structures 152. Such bungees or other elastomeric linkages may provide a cross-cross or zig-zag connection, providing assistance with extension movement of the knee, providing POST, and potentially aiding in providing the upward, angular lines or strap structure described in Applicant's provisional filings which may promote circulation of blood and other body fluids (e.g., through the lymph structures), edema management, and the like. An addition example of such criss-cross, upwardly extending or angling support geometry is shown in the straps 106 of FIG. 7. In an embodiment, such straps may be elastomeric, so as to provide variable tension about the knee and leg of the user.

Figure 16:
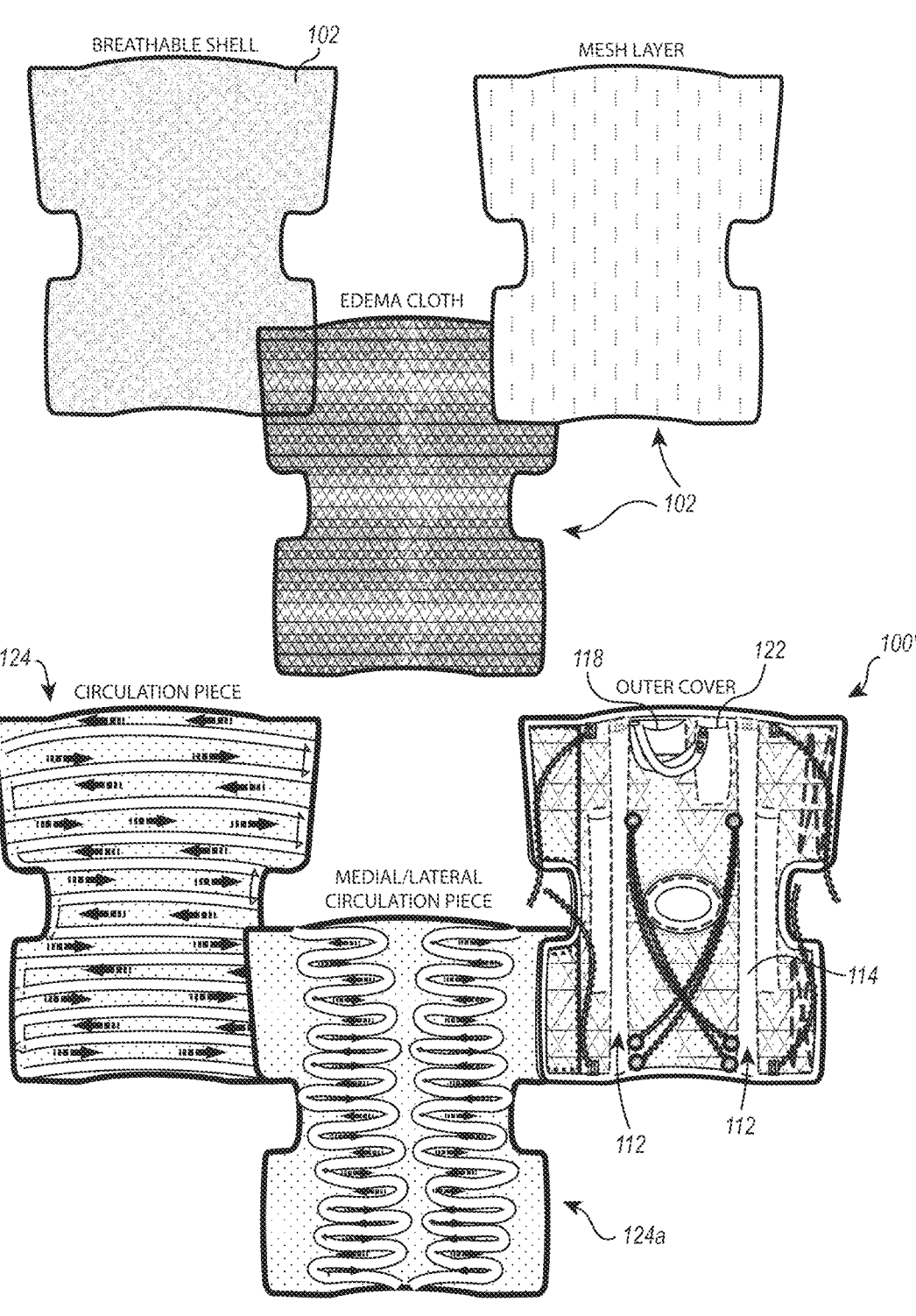
FIG. 16 schematically illustrates how the knee brace may include multiple layers, which may be selected for inclusion into the knee brace itself, so as to provide desired benefits.

FIG. 16 illustrates another combination of various layers and or structures that may go into the knee brace, e.g., similar to those shown in FIGS. 5A-5D and 6A-6D. The two circulation pieces 124, 124*a* (particularly 124*a*) shows how the circulation coils may be configured to provide increased coil density to certain areas (e.g., medial/lateral regions), as compared to other regions, if it is desired to direct additional heating or cooling to particular regions surrounding the knee.

Figure 17:
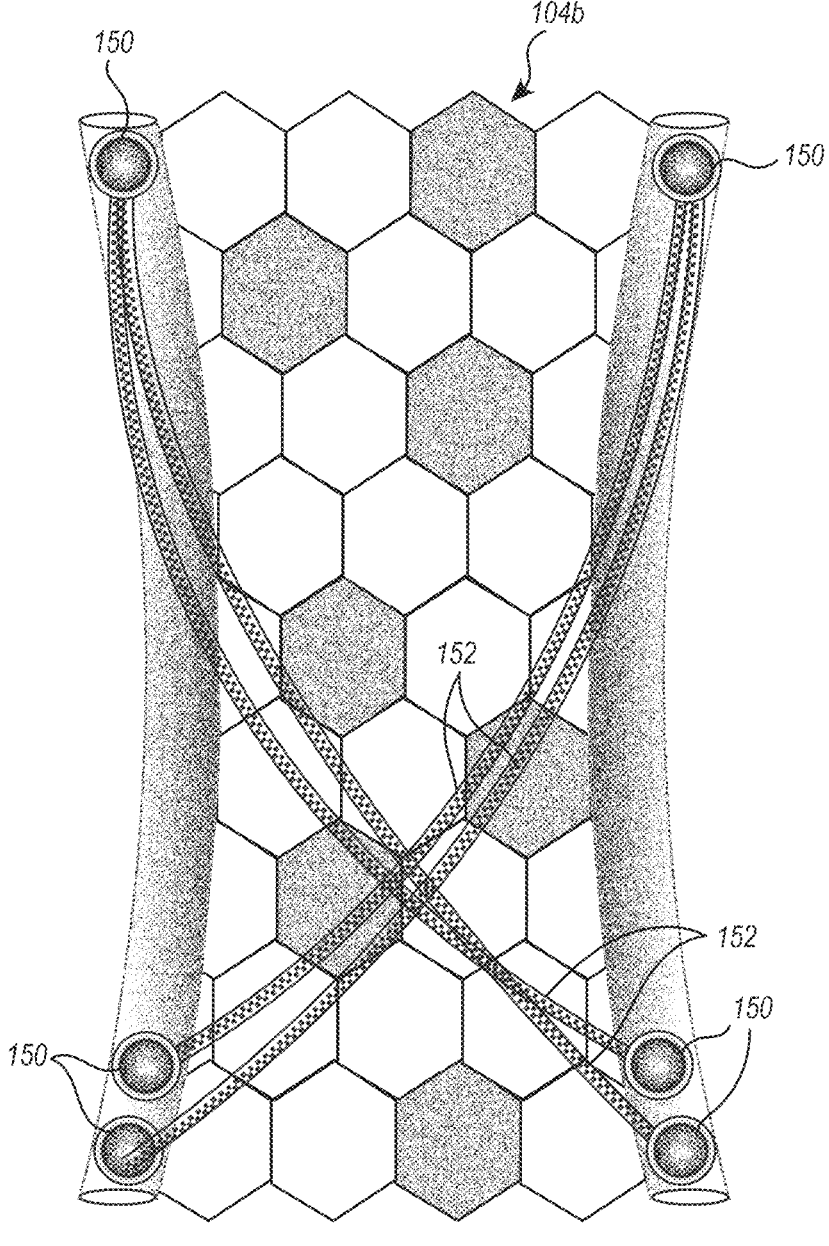
FIG. 17 schematically illustrates an exemplary exoskeleton piece of the knee brace, with geometric hexagonal honeycomb structure, also showing elastic bungees in a criss-cross arrangement.

FIG. 17 illustrates bungees or elastomeric straps 152 in combination with an exoskeleton or other directional stability providing structure, 104*b* (e.g., similar to FIG. 13A), showing how the bungee anchors 150 could themselves be anchored to particular structure of the knee brace outer cover 100'. While shown with one particular directional geometry structure (e.g., 104*b* of FIG. 13A), it will be appreciated that any of the directional geometry structures described herein (or others) could alternatively be used.

FIGS. 18A-19 illustrate an exemplary portable elevation stand that may be provided as one of the modules for use with the knee brace, as part of the overall system. Such an elevation stand may be configured as a tripod 154, as shown, or as a bipod, a monopod, or other support structure for elevating the lower leg of the user above the ground, e.g., during resting, and while providing full terminal extension to the user's knee. FIG. 18A illustrates a cradle 156 which may be provided with such elevation stand, for easily receiving and/or attaching to the knee brace. FIG. 18B illustrates how such a cradle and/or elevation stand could include a ball joint 158 or other joint providing the user with the ability to move their leg, while it is resting within such a cradle 156, or otherwise supported by elevation stand 154. FIG. 19 shows how the elevation stand 154 may be collapsible, allowing it to easily be placed within backpack 160 of FIG. 20, for example. For example, the legs of elevation stand 154 may telescope, for easy storage and transport. The ball joint 158 may be selectively removable from the stand 154, e.g., allowing it to be easily popped in and out, as needed for use. The shell 102 of the knee brace may have a ball joint connector plate sewn or otherwise integrated therein, to mate to the ball joint, or a portion of the ball joint connector (e.g., a portion of the ball joint could be in the stand, and another portion in the shell 102, allowing the user to easily and quickly connect the two together, with the brace attached to the stand by the ball or other joint). The cradle 156 may be a half cylindrical or half-conical shape to allow the calf or back of the knee to comfortably fit therein while the brace is attached to or resting in the elevation stand.

In addition to storing stand 154, backpack 160 could similarly be used to store and carry the various other modular components of the system, such as the pump the canister or other reservoir, any of the various described stiffener inserts, or the like. The modularity of the system allows a user to mix and match those components that they select for use with the knee brace, at any given time, e.g., taking those components they wish to use with them, while leaving the other components at home, the office, etc.

The system may thus be portable, mobile, to be used at home, school, office, on public transportation, etc. For example, such a portable system could be used immediately following a trip to the fitness or yoga studio, physical therapy, MD appointment, or while traveling.

A mindfulness program that offers awareness to stress management, instruction in breathing techniques, and basic yoga postures that can be done seated or lying down may be provided therewith.

Exemplary AI Custom Components

In some embodiments, the present invention uses artificial intelligence (AI) recommended custom components as well as machine learning (ML) algorithms and/or neural networks. The system may use a diagnostic algorithm, a real-time algorithm, a post treatment algorithm, or a combination thereof. The details of the models may be accessible on a hospital computer, personal computer, or application created for smart devices. The model and results may be shown in a graphical user interface (GUI). The GUI may be optimized to show the same or different results to medical professionals and the patient. More detail about each algorithm will be described in more detail herein.

During the initial customization and configuration phase of the brace for each unique patient, the AI framework may be used to optimize the brace based on the patient's unique treatment plan, health history/profile, diagnosis, and/or other applicable factors. As therapy continues and the patient continues to heal, the AI may monitor the progress and suggest treatment options and plans to doctors, nurses, physical therapists, and other medical professionals. Additionally, the AI may inform the patient themselves, or the patient's caregiver, of suggested treatments that can be performed independently. The suggested treatment can also be used by the patient and/or caregivers of the patient to better assist in the healing/therapy process. The brace can further be reconfigured to optimize treatment based on the suggested recommendations.

Some embodiments utilize a diagnostic AI/ML/neural network algorithm. For example, the model may be trained by the following procedure. The train begins by taking into account a number of input values (also known as considerations) and multiplying the input values by weights. The multiplied values may be summed to create a weighted sum. The weighted sum may be applied to an activation function which results in an output (also known as a determination). The weights may be calibrated so that an expected determination/output is achieved when applying the considerations/inputs to the model.

Figure 21:
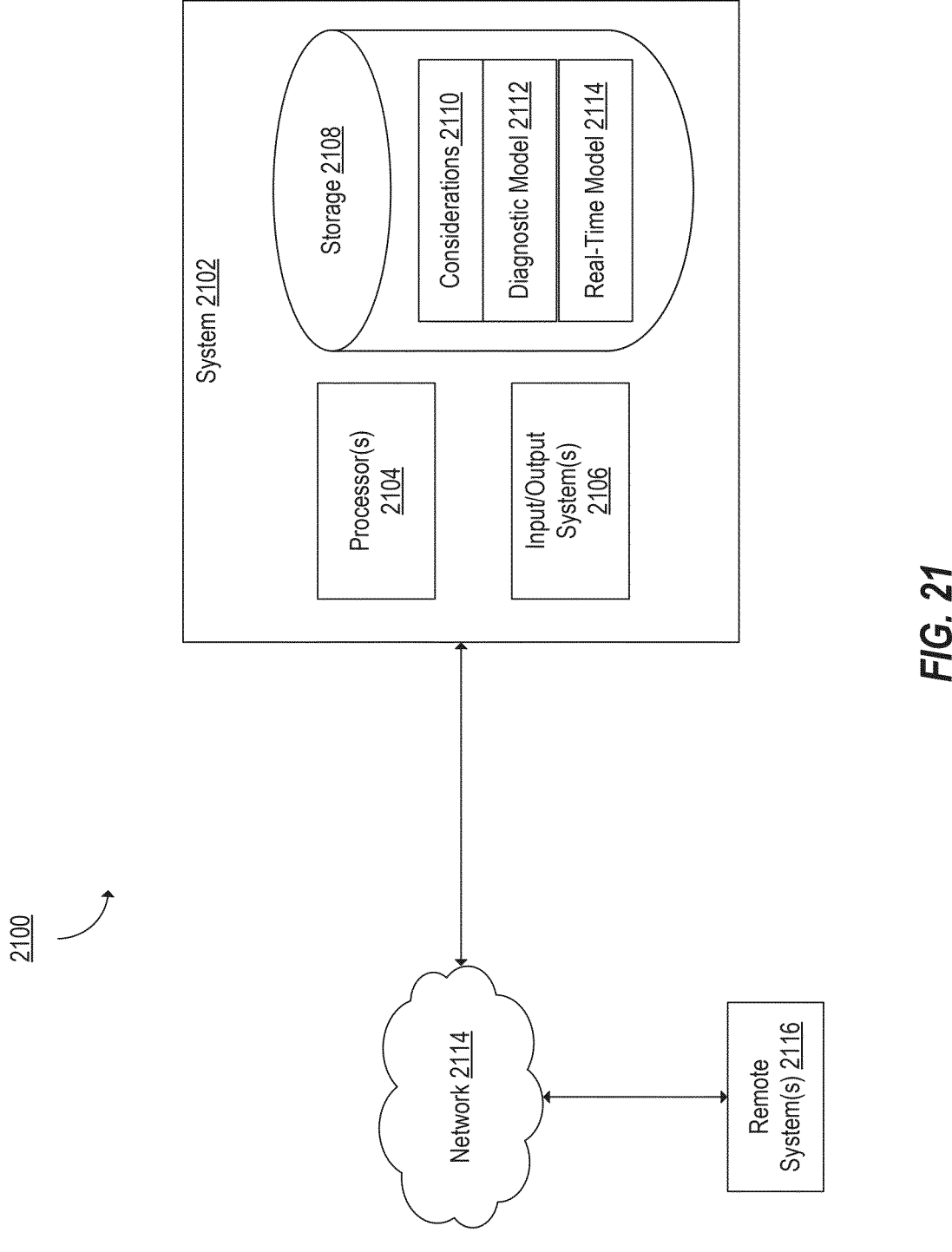
FIG. 21 illustrates an example computing system.

FIG. 21 illustrates an example of a computing system 2100 that can be used in embodiments that utilized the diagnostic model 2112 and/or the real-time model 2114. The computing system 2100 may include one or more processor 2104 and one or more hardware storage devices 2108 storing computer executable instructions, such as input data (considerations 2110) and models such as the diagnostic model 2112 and the real-time model 2114, that, when executed by the one or more processers 2104, cause the computing system to perform the functionality described. The computing system 2100 may additionally include one or more input/output systems 2106 and one or more remote systems 2116 which may be connected to the system 2102 by a network 2114.

Figure 22:
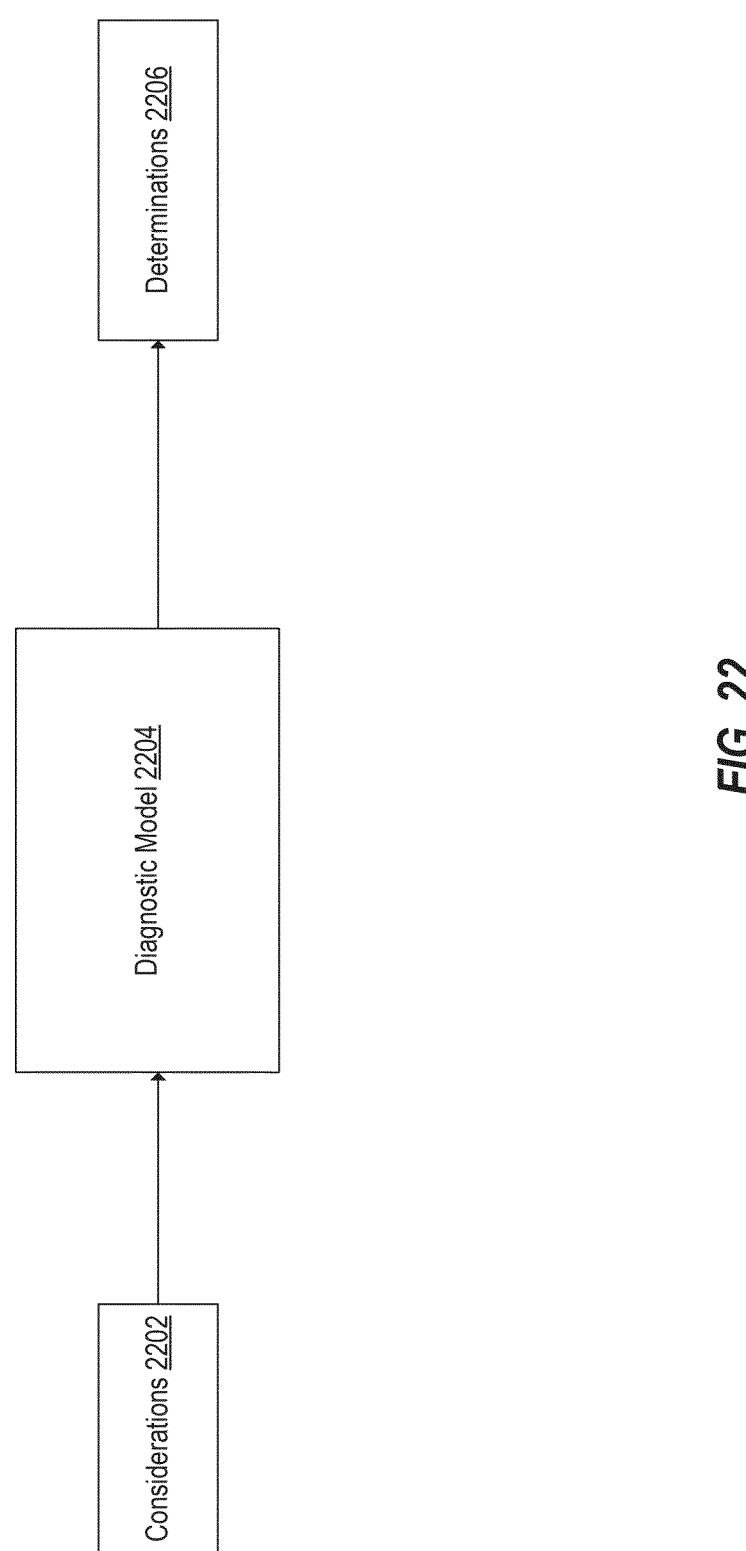
FIG. 22 illustrates an example runtime of a diagnostic model.

FIG. 22 illustrates an example runtime environment for the diagnostic model 2204. Considerations 2202 are used as input in the trained diagnostic model 2204. The diagnostic model 2204 then outputs determinations 2206 which may be used to create the knee brace.

Some examples of considerations 2202 for the diagnostic model 2204 may include some or all of the following factors: medical history, diagnostics performed, treatments performed, body mass index (BMI), edema management custom 3D prints, thermal management, stimulus therapy, lymphatic massage, balance scores, walk tests, electromyograph (EMG), TENS, ground reaction response, infrared technology, assistive devices, knee girth, performance, stability, length of limb, osteoarthritis score, muscle force absorption, ligament laxity, drop lock therapy, patella exam, posture, and physical activity. More details about each consideration are now described.

Medical history may be general history or particular history relating to an injury or surgery. Diagnostic tests may include known or pending x-rays, MRIs, ultrasounds, or arthrograms with contrast. Previously performed treatments may include cortisone, stem cells, or cartilage treatment injections. Patient measurements such as body mass index (BMI), weight, age, gender, and height. Custom 3D prints may include 3 categories of rigidity and strength while allowing movement in the frontal plane, the sagittal plane, and the transverse plane. Custom 3D prints may also include minimal stability (e.g., no movement), moderate stability (e.g., pivoting), or maximum stability (running, pivoting, change in direction, jumping, and contact related sports).

Treatment management may include edema management (e.g., degree grade 1, 2, or 3 and pitting edema) and thermal management (e.g., heating or cooling). Stimulus therapy includes localized vibrations for sub-cutaneous C-fiber and/or pain receptor reduction. Massage therapy may include lymphatic massages. A balance score includes static or dynamic balance based on an objective assessment (e.g., BERG balance score, TUG test, or other functional tests). Walk tests may include distance, speed, type of assistances, rests, and gait of walks over a specified time period (e.g., 6 minutes). Electromyograph (EMG) results may include muscle groups and activity. Ground reaction response may include normal or abnormal patterns by measuring gait, posture, alignment, limp, and/or other asymmetries.

Assistive devices include whether cane(s), crutch(es), walker(s), rolling walker, wheelchair, scooter, non-weight bearing scooter, or other assistive devices are used. Knee girth includes the measurement of girth at the knee cap, above the knee cap (e.g., 6 inches above), below the knee cap (e.g., 6 inches below the knee cap), and at the ankle joint. Performance includes low load long duration stretch for different time intervals (e.g., 30 seconds, 1 minutes, 5 minutes, 6 minutes, 7 minutes, or 8 minutes). Stability includes tests such as Lachman, Anterior Draw, McMurray's.

The length of the limb includes from the hip to ankle joint (e.g., are both legs symmetrical). Osteoarthritis score includes results from the Kellgren Lawrence Osteoarthritis Classification include score grades of 0, 1, 2, 3, and 4 as well as if the osteoarthritis is medial, lateral, or both. Treatment may vary depending on the score of the Kellgren Lawrence Osteoarthritis Classification. For example, if a patient scores a 1, minimal therapy may be required, however, if a patient scores a 5, heat and support may be applied much more frequently. Muscle force absorption includes fluid swing phase measurements and stance phase of gait due to excess limb loading, lack of swing, excess stance time, heal strike, foot flat, or toe off. Ligament laxity includes the knee joint hyper mobility.

Drop lock therapy includes the locking out of a brace for surgery protocol, healing after surgery, cartilage repair or protocols that inhibit flexion and/or extension or hyper extension. Patella exam includes results of knee cap pain, asymmetry, or dislocation. Posture includes valgus, varus, or normal posture. Physical activity includes participation in exercise and/or sports as well as duration and frequency.

Some examples of determinations 2206 for the diagnostic model 2204 may include some or all of the following outputs: compression requirement, compression level, frequency of application, duration of cation throughout the day, lymphatic massage, TENS, electromyograph (EMG). More details about each consideration are now described.

Compression requirement and level may include the degree of compression indicated for the treatment. Frequency of application may include during the day, night, day and night, or some other amount of time. Duration of cation may include during the day, night, day and night, or some other amount of time. Lymphatic massage and TENS may include the frequency and duration of the treatment. EMG may include determining the level (e.g., low tone, weakness) and/or minimizing or inhibiting treatment (e.g., hypertonic, spasticity, contractures).

Figure 23:
FIG. 23 illustrates an example of integrated modules in an exemplary knee brace.
Figure 23:

FIG. 23 illustrates example modules that can be incorporated into the knee brace based on determinations from the diagnostic model. The modules may include thermal modules 2302, motive modules 2304, environment modules 2306, tactile modules 2308, light modules 2310, structural modules 2312, other applicable modules, or a combination of one or more modules.

The thermal modules 2302 may include heating, cooling, and humidity modules. The motive modules 2304 may include accelerometers, gyroscopes, and e-compasses. The environment modules 2306 may include proximity and pressure modules. The tactile modules 2308 may include ultrasounds, e-stimulators, and vibrations. The light modules 2310 may include LED and infrared lights. The structural modules 2312 may include support, protective, and flex modules.

Each different therapy module may be mapped in a module map to align in shape to zones of therapy in the knee region. Example therapy zones may include a patellar region, quad region, medial region, lateral region, anterior region, posterior region, or other regions around the knee.

The sensors and/or various modes of therapies incorporated in the modules are intended to be interchangeable. This allows for reconfiguration of the brace, including the incorporated modules, in response to determinations from a real-time module as therapy/treatment progresses. The real-time module is described in more detail below.

Figure 24:
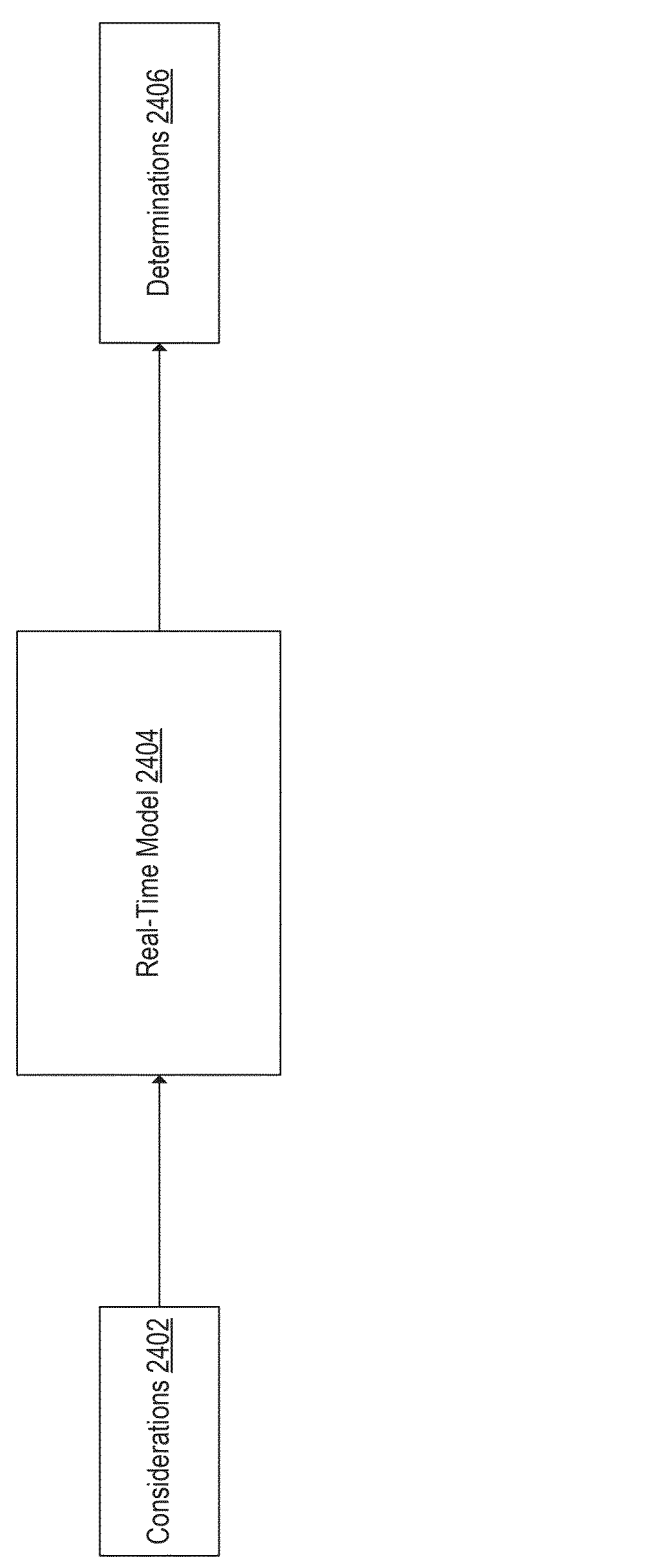
FIG. 24 illustrates an example runtime of a real-time model.

FIG. 24 illustrates an example runtime environment for the real-time model 2404. Considerations 2402 are used as input in the trained real-time model 2404. The real-time model 2404 then outputs determinations 2406 which may be used to reconfigure, modify, and/or dynamically tune the knee brace.

In more detail, some embodiments of the invention may further include a real-time AI/ML/neural network model to collect raw real-time data from embedded sensors in the brace. The sensors in the brace may be connected to a BLE Mesh network or similar wireless network which is further connected to an application accessible on electronic devices (e.g., smart computing devices, smart phones, computers, medical equipment, etc.). The embedded sensors may include accelerometers, thermistors, altimeters, gyroscopes, EKGs, gait measuring devices, or other measuring devices to collect data while a patient wears the brace. The real-time algorithm may be utilized by the patient and/or patient caregiver as well as physical therapists, doctors, nurses, or other medical professionals. The real-time model may be used retroactively, during therapy, or while active monitoring to optimize, manage, design, and/or determine proper treatment.

Some examples of considerations 2402 for the real-time model 2404 may include some or all of the following factors: range of motion detection, joint fault detection, ground reaction response, arthrokinematics detection, weight bearing detection, muscle force absorption, and ligament laxity. More details about each consideration are now described.

Range of motion detection may include monitoring full range of motion, limited range of motion, or lock modes. Joint fault detection may include buckling of the knee joint and/or occurrences, frequencies, and severities of falls. Ground reaction response may include normal or abnormal patterns measured by gait deviation, posture, alignment, limp, and other asymmetries. Arthrokinematics detection includes arthrokinematics during knee extensions in exercises such as screw home mechanisms, quad sets, isometric exercises, or other key movements. Weight bearing detection may include how weight bearing is tolerated (e.g., NWB, TTWB, PWB for loading and healing tendons) and functional mobility, exercise, and gait. Muscle force absorption may include the fluid wing phase and stance phase of gait as well as dysfunction of excess limb loading, lack of swing, excess stance time, paint during swing phase, heal strike, foot flat, and toe off. Ligament laxity may include the knee joint hyper mobility.

The real-time algorithm 2404 may output a determination 2406 based on knee faults. The knee fault determination may include the need for an immediate therapeutic response based off of predictions of the real-time algorithm given the considerations.

The real-time algorithm may also be used to remote monitor the patient to determine whether the brace is effectively being used and aiding in treatment. The remote monitoring may be performed by caregivers, doctors, nurses, physical therapists, or other medical professionals. The remote monitoring may include determining whether the patient is following through with the assigned treatment plan such as compression, cooling, heating, appropriate weight bearing, range of motion, or other treatments.

Figure 25:
FIG. 25 illustrates a flow chart of acts associated with creating a knee brace.

FIG. 25 illustrates a flow chart 2500 of various acts associated with embodiments of the invention which utilize the diagnostic model to create custom knee braces associated with unique patients.

The method first accesses a diagnostic model (act 2502) and obtains a set of considerations (act 2504) to input into the trained diagnostic model. The set of considerations are applied to the diagnostic model (act 2506) and the diagnostic model outputs a set of determinations (act 2508). The set of determinations are then used to create a customized knee brace based on the set of determinations (act 2510).

Figure 26:
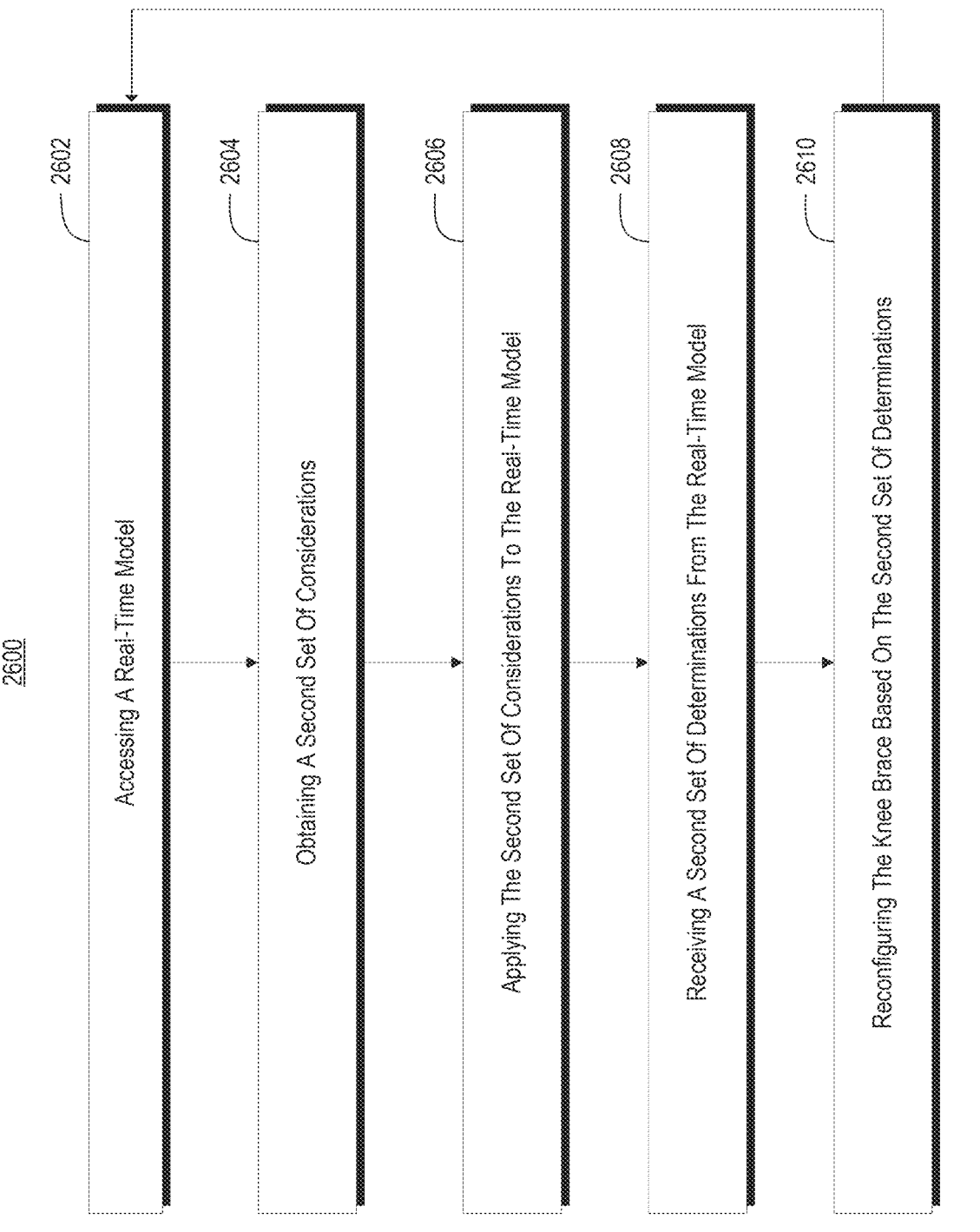
FIG. 26 illustrates a flow chart of acts associated with reconfiguring a knee brace.

FIG. 26 illustrates a flow chart 2600 of various acts associated with embodiments of the invention which utilize the real-time model to reconfigure the custom knee brace.

The method first accesses a real-time model (act 2602) and obtains a second set of considerations (act 2604) to input into the trained real-time model. The second set of considerations are applied to the real-time model (act 2606) and the real-time model outputs a second set of determinations (act 2608). The second set of determinations are then used to reconfigure the knee braced based on the second set of determinations (act 2610). The reconfiguration processes may iterate continuously by accessing the real-time model (act 2602) and beginning the reconfiguration process again. The process may continue until the brace is properly optimized. Some embodiments may use the real-time model to reconfigure the brace and then use the real-time model after some amount of time has passed to reconfigure the brace based on the patient's specific needs at a future time.

In some embodiments, the disclosed invention does not perform the RICE treatment (rest, ice, compression, elevation). Some embodiments do not provide or perform scaffolding. In particular, some embodiments may include some minor scaffold structures, although that will not be the only, or primary purpose and function provided by a brace according to the present disclosure. Some embodiments do not perform stationary therapeutic treatments. Some embodiments are void of aluminum. Some embodiments do not include purely isolated structural side supports. Some embodiments do not include a stationary tripod with pockets for ice packs. Some embodiments do not include a hinge in the tripod. Some embodiments do not include pads. Some embodiments do not include a set number of fixed pads. Some embodiments are not a limb positioner, multi-axis locking positioner mechanism for passive elevation, or positioning for surgery. Some embodiments are not mounted to furniture such as a hospital bed. Some embodiments do not include a locking mechanism for fixed mechanical support including bolt/screw methods. Some embodiments do not provide hot and/or cold stationary therapy. Some embodiments do not include a rigid, fixed, supportive holding device.

In contrast to US 2010/0057171 to Stephens, in an embodiment, the present invention does not include any bulky tripod, particularly with a knee support member provided at the top of such tripod, having a U-shaped cross-section for receiving the knee of the user. Such a configuration is bulky, not portable, and fixed, while the present invention in contrast provides knee braces or other joint braces that are portable, intended to be worn while the user is in motion, while bending such joint, etc. While in an embodiment some type of support structure may be provided, this will not be a rigid, fixed tripod, but e.g., perhaps a removable lightweight, small kickstand type structure, if it is desired to raise the knee up during a period of rest. Furthermore, while Stephens includes a pouch within the knee support member of the tripod, for receipt of an icepack or heat pack, in an embodiment, no such pouch is provided with any support (e.g., kickstand) associated with the present invention. Unlike the presently contemplated knee brace, the cradle in Stephens cannot be worn separately from the tripod, to provide heat or cooling therapy. The tripod and the cradle are required to be assembled together to make the device function. In particular, in the present invention, if any pouches are provided for insertion of ice packs or heat packs, such may be provided with the knee brace or other brace itself, and can be used without the presence or need for any tripod, kickstand, or other support. Furthermore, in an embodiment, any of the objects or features of Stephens' invention as identified in Stephens, may be absent from the present invention.

In contrast to US 2014/0222121 to Spence, in an embodiment, the present invention does not include any garment, that would cover any portion of the body, other than a knee joint, or similar joint (e.g., elbow). For example, the present invention, in an embodiment, does not provide coverage for any portion of the users torso, upper legs (e.g., thighs), calves, ankles, etc.). Furthermore, in an embodiment, the present invention does not provide any type of pad for heating or cooling body parts (other than to the knee or other joint). No such pad including first and second flexible layers is provided, in an embodiment. Furthermore, in an embodiment, any of the objects or features of Spence's invention as identified in Spence, may be absent from the present invention.

In contrast to U.S. Pat. No. 8,425,579 to Edelman, in an embodiment, the present invention does not include fixed knee brace, configured to immobilize the knee. Rather, the present embodiments are intended to be worn while the user is in motion, bending their knee, providing some support to the knee, but certainly not immobilizing the knee, as in Edelman. Edelman discloses a continuous passive motion device that is configured to cause a patient's knee to continuously move passively. FIG. 10A of Edelman illustrates an example of a continuous passive motion device. Such a continuous passive motion device is designed to be fairly heavy duty and stationary, which is opposite to the presently contemplated portable, light-duty knee brace. Furthermore, in an embodiment, any of the objects or features of Edelman's invention as identified in Edelman, may be absent from the present invention.

In contrast to US 2014/0330184 to Kilbey, in an embodiment, the present invention does not include any internal air bladder for inflation, e.g., to secure fit of a large wrap, which fits over the front of the leg, for wrapping around the knee. Furthermore, while the present invention may include one or more removable relatively rigid (or semi-rigid) inserts, in an embodiment, such inserts are not configured to hold the knee so that it cannot flex or extend, as in Kilbey. The inserts serve an entirely different function, by providing support and stability to the lateral and medial portions of the knee, but they do not prevent flexion or extension of the knee, as Kilbey teaches. In the present invention, the one or more elastic elongate linkage structures configured to attach to the plurality of attachment points to form a criss-cross or a zig-zag connection (see FIG. 17) provide support and fit, along with the lateral and medial inserts. Such inserts do not prevent flexing or extension of the knee, as in Kilbey. Also in contrast to Kilbey the plurality of elastic elongate linkage structures of the present invention are attached to corresponding attachment points to form criss-cross or zig-zag connections of the elastic elongate linkage structures positioned in a medial portion of the breathable shell layer, so as to be stabilize a tibia of the user. No such placement or function is provided or even possible in Kilbey. Furthermore, in an embodiment, any of the objects or features of Kilbey's invention as identified in Kilbey, may be absent from the present invention.

Any of the objects, or features of any of U.S. Pat. No. 7,959,657 to Harsy, US2007/0161932 to Pick, US2015/0290014 to Anglada, US2010/0018537 to Soto and/or US2012/0290102 to Mahoney, as identified in any such references, may be expressly absent from embodiments of the present invention. Each of such references are expressly incorporated herein by reference in their entirety, as well as any other references specifically referenced herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of creating a portable knee brace system for use in recovery after injury or surgery, the method comprising:

accessing a diagnostic model;

obtaining a set of considerations;

applying the set of considerations to the diagnostic model;

receiving a set of determinations from the diagnostic model; and creating a modular knee brace, comprising one or more separable and selectable layers, based on the set of determinations, the knee brace comprising:

a breathable shell layer configured to provide support around the knee of a user;

a geometric structure that provides directional stability, the geometric structure being sewn or otherwise integrated into one of the one or more separable and selectable layers, the geometric layer having a form of at least one of a geometric matrix or lattice; and cooling means provided in the knee brace for providing coolant to the knee brace to reduce inflammation in the knee of the user; and wherein one or more characteristics of the knee brace as constructed are customized to an individual user based on the diagnostic model, the set of considerations, and the set of determinations.

2. The method as recited in claim 1, wherein the cooling means comprises tubing provided in the knee brace for carrying a coolant pumped from a coolant pump and reservoir to which the pump and the reservoir are selectively coupleable to the tubing of the knee brace to circulate coolant therethrough.

3. The method as recited in claim 2, wherein the tubing provided in the knee brace is of a lay-flat configuration so as to be configured to lay flat when no coolant is being circulated therethrough.

4. The method as recited in claim 2, wherein the knee brace further comprises the coolant pump and reservoir for pumping coolant into the tubing of the knee brace, wherein the coolant pump and reservoir are portable.

5. The method as recited in claim 4, wherein the coolant pump and reservoir are provided (i) within a backpack that is wearable by the user or (ii) in pockets positioned in the knee brace.

6. The method as recited in claim 4, wherein the coolant pump or a heating mechanism for selectively delivering heat to the knee of the user is powered by a compact rechargeable battery.

7. The method as recited in claim 1, wherein the modular knee brace further comprises an elevation stand configured for selective attachment to the knee brace to allow the user to elevate the knee of the user when the elevation stand is attached thereto.

8. The method as recited in claim 7, wherein the knee brace further comprises a coupling mechanism for selectively coupling the elevation stand to the knee brace, wherein the coupling mechanism comprises a ball joint.

9. The method as recited in claim 1, wherein the knee brace further comprises a heating mechanism for selectively delivering heat to the knee of a user.

10. The method as recited in claim 1, wherein the geometric structure is a removable insert that is receivable in a corresponding receiving pocket in the knee brace, the insert being selectively insertable into the receiving pocket to full terminal extension of the knee when the insert is inserted into the receiving pocket of the knee brace.

11. The method as recited in claim 1, the knee brace further comprising elastic support straps attached to the breathable shell layer, wherein the elastic support straps are engageable in a criss-cross arrangement extending upwardly relative to a leg of the user when the knee brace is worn.

12. The method as recited in claim 1, wherein the breathable shell layer provides at least one of medial, lateral, anterior, posterior, tension or flexion support with directional stability.

13. The method as recited in claim 12, wherein the directional stability provides resistance against at least one of:

knee torsion;
  medial knee movement,
  lateral knee movement; or
  knee flexion, such that the directional stability is configured to provide a bias towards knee extension.

14. The method as recited in claim 1, wherein the set of considerations includes at least one of: medical history, diagnostics performed, treatments performed, BMI, edema management custom 3D prints, thermal management, stimulus therapy, lymphatic massage, balance scores, walk tests, EMG, TENS, ground reaction response, infrared technology, assistive devices, knee girth, performance, stability, length of limb, osteoarthritis score, muscle force absorption, ligament laxity, drop lock therapy, patella exam, posture, or physical activity.

15. The method as recited in claim 1, wherein the set of determinations includes at least one of: compression requirement, compression level, frequency of application, duration of cation throughout the day, lymphatic massage, TENS, or EMG.

16. The method as recited in claim 1, further comprising:
  accessing a real-time model;
  obtaining a second set of considerations;
  applying the second set of considerations to the real-time model;
  receiving a second set of determinations from the real-time model; and
  reconfiguring the knee brace based on the second set of determinations.

17. The method as recited in claim 16, wherein the second set of considerations includes at least one of: range of motion detection, joint fault detection, ground reaction response, arthrokinematics detection, weight bearing detection, muscle force absorption, or ligament laxity.

18. The method as recited in claim 16, wherein the second set of determinations includes knee faults.

19. The method as recited in claim 16, further comprising:
  sending the second set of determinations to a health professional.

20. The method as recited in claim 1, wherein the geometric structure is a removable insert comprising a closed edge, the closed edge extending between one or more pods, the removable insert further comprising thin living hinges, and wherein the thin living hinges comprise a compliant mechanism and extend from the closed edge and extend towards an open edge of the removable insert.

21. The method as recited in claim 1, wherein the geometric structure comprises one or more two-part geometric shapes, wherein a first portion of a first two-part geometric shape slidably engages with a second portion of the first two-part geometric shape to allow for directional compression movement.

22. The method as recited in claim 7, wherein the elevation stand is configured as a monopod, a bipod, or a tripod.

* * * * *